(12) United States Patent
Adessi et al.

(10) Patent No.: US 10,370,652 B2
(45) Date of Patent: *Aug. 6, 2019

(54) METHODS OF NUCLEIC ACID AMPLIFICATION AND SEQUENCING

(71) Applicants: Illumina, Inc., San Diego, CA (US); Illumina Cambridge Limited, Essex (GB)

(72) Inventors: Celine Adessi, Ambilly (FR); Eric Kawashima, Nyon (CH); Pascal Mayer, Eloise (FR); Jean-Jacques Mermod, Geneva (CH); Gerardo Turcatti, Geneva (CH)

(73) Assignee: Illumina, Inc., San Diego, CA (US)

( * ) Notice: Subject to any disclaimer, the term of this patent is extended or adjusted under 35 U.S.C. 154(b) by 236 days.

This patent is subject to a terminal disclaimer.

(21) Appl. No.: 15/050,345

(22) Filed: Feb. 22, 2016

(65) Prior Publication Data
US 2016/0319274 A1 Nov. 3, 2016

Related U.S. Application Data

(63) Continuation of application No. 14/150,607, filed on Jan. 8, 2014, now Pat. No. 9,297,006, which is a continuation of application No. 11/506,146, filed on Aug. 17, 2006, now Pat. No. 8,652,810, which is a continuation of application No. 09/806,531, filed as application No. PCT/GB99/03248 on Sep. 30, 1999, now Pat. No. 7,115,400.

(30) Foreign Application Priority Data

Sep. 30, 1998 (EP) .................................. 98307985

(51) Int. Cl.
| | | |
|---|---|---|
| *C12P 19/34* | (2006.01) | |
| *C12N 15/10* | (2006.01) | |
| *C12Q 1/6837* | (2018.01) | |
| *C12Q 1/686* | (2018.01) | |
| *C12Q 1/6869* | (2018.01) | |
| *C12Q 1/6874* | (2018.01) | |

(52) U.S. Cl.
CPC ......... *C12N 15/1068* (2013.01); *C12Q 1/686* (2013.01); *C12Q 1/6837* (2013.01); *C12Q 1/6869* (2013.01); *C12Q 1/6874* (2013.01)

(58) Field of Classification Search
USPC .......... 435/6.1, 6.11, 6.12, 91.1, 91.2, 91.51, 435/183; 436/94, 501; 536/23.1, 24.3, 536/24.33, 25.3
See application file for complete search history.

(56) References Cited

U.S. PATENT DOCUMENTS

| | | |
|---|---|---|
| 5,326,692 A | 7/1994 | Brinkley et al. |
| 5,436,142 A | 7/1995 | Wigler et al. |
| 5,508,169 A | 4/1996 | Deugau et al. |
| 5,514,539 A | 5/1996 | Bukh et al. |
| 5,547,839 A | 8/1996 | Dower et al. |
| 5,616,478 A | 4/1997 | Chetverin |
| 5,629,158 A | 5/1997 | Uhlen |
| 5,753,439 A | 5/1998 | Smith et al. |
| 5,830,663 A | 11/1998 | Embleton et al. |
| 5,922,574 A | 7/1999 | Minter |
| 5,939,291 A | 8/1999 | Loewy et al. |
| 6,060,288 A | 5/2000 | Adams et al. |
| 6,107,023 A | 8/2000 | Reyes et al. |
| 6,218,142 B1 | 4/2001 | Wassenegger et al. |
| 6,280,949 B1 | 8/2001 | Lizardi |
| 6,316,229 B1 | 11/2001 | Lizardi et al. |
| 6,322,971 B1 | 11/2001 | Chetverin et al. |
| 6,326,489 B1 | 12/2001 | Church et al. |
| 6,406,893 B1 | 6/2002 | Knapp et al. |

(Continued)

FOREIGN PATENT DOCUMENTS

| | | |
|---|---|---|
| EP | 0 224 126 | 6/1987 |
| EP | 0 356 021 | 2/1990 |

(Continued)

OTHER PUBLICATIONS

Answers.com, "Universal Primers", The definition of "universal primers" from answers.com. Printed on Aug. 6, 2013.

(Continued)

*Primary Examiner* — Frank W Lu
(74) *Attorney, Agent, or Firm* — Mueting, Raasch & Gebhardt, P.A.

(57) ABSTRACT

Methods for amplification and sequencing of at least one nucleic acid comprising the following steps: (1) forming at least one nucleic acid template comprising the nucleic acid(s) to be amplified or sequenced, wherein said nucleic acid(s) contains at the 5' end an oligonucleotide sequence Y and at the 3' end an oligonucleotide sequence Z and, in addition, the nucleic acid(s) carry at the 5' end a means for attaching the nucleic acid(s) to a solid support; (2) mixing said nucleic acid template(s) with one or more colony primers X, which can hybridize to the oligonucleotide sequence Z and carries at the 5' end a means for attaching the colony primers to a solid support, in the presence of a solid support so that the 5' ends of both the nucleic acid template and the colony primers bind to the solid support; (3) performing one or more nucleic acid amplification reactions on the bound template(s), so that nucleic acid colonies are generated and optionally, performing at least one step of sequence determination of one or more of the nucleic acid colonies generated. Solid supports, kits and apparatus for use in these methods.

16 Claims, 10 Drawing Sheets

Figure 1:
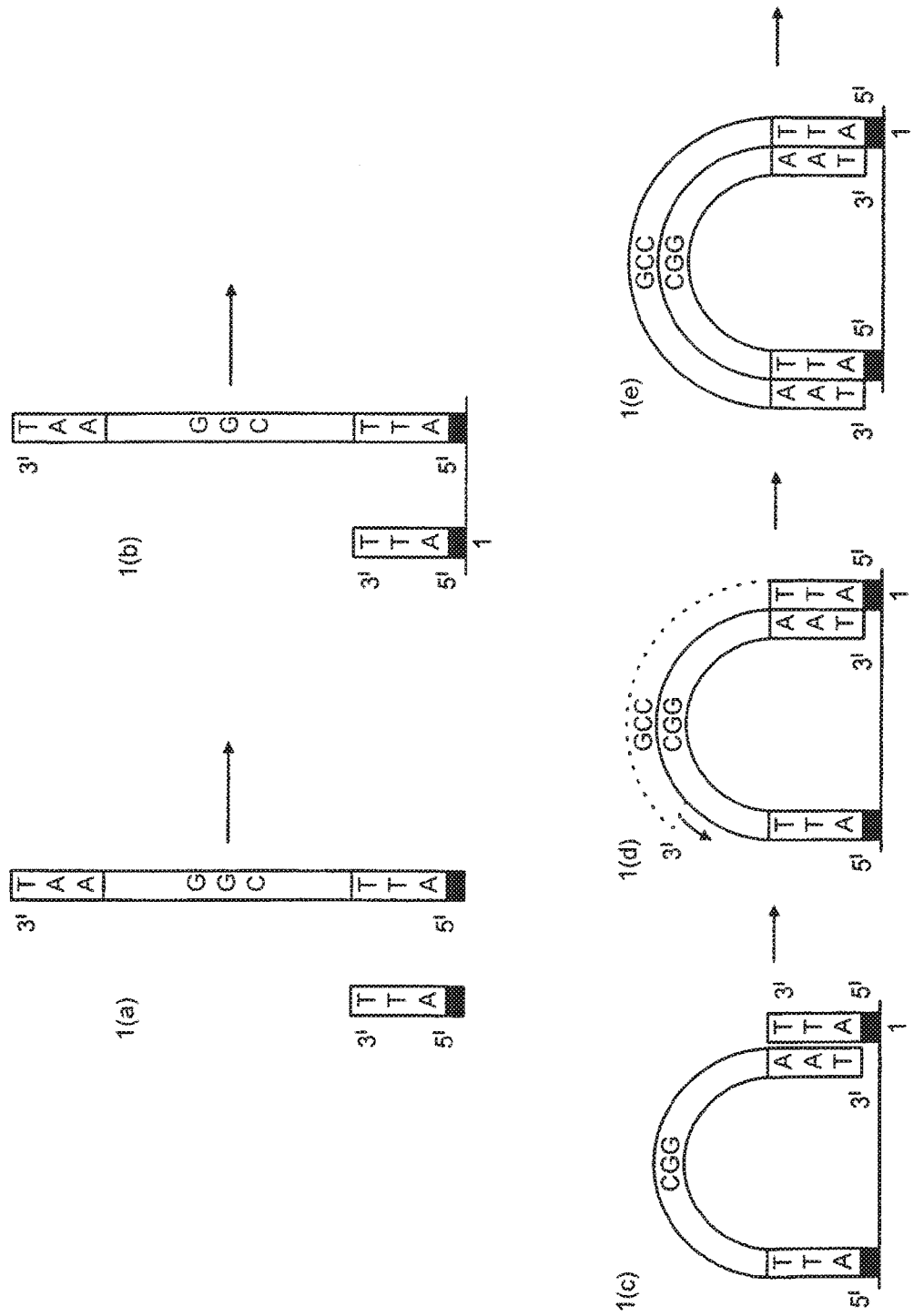

Specification includes a Sequence Listing.

(56) References Cited

U.S. PATENT DOCUMENTS

| | | |
|---|---|---|
| 6,432,680 B1 | 8/2002 | Lin et al. |
| 6,489,103 B1 | 12/2002 | Griffiths et al. |
| 6,511,803 B1 | 1/2003 | Church et al. |
| 7,115,400 B1 | 10/2006 | Adessi et al. |
| 8,652,810 B2 | 2/2014 | Adessi et al. |
| 9,297,066 B2 | 3/2016 | Adessi et al. |
| 2005/0100900 A1 | 5/2005 | Kawashima et al. |

FOREIGN PATENT DOCUMENTS

| | | |
|---|---|---|
| EP | 0 374 665 | 6/1990 |
| EP | 0543484 | 5/1993 |
| EP | 0 665 293 | 8/1995 |
| EP | 0 763 135 | 3/1997 |
| EP | 1 019 496 | 7/2000 |
| EP | 1 482 036 | 12/2004 |
| EP | 1117827 | 11/2005 |
| WO | WO 87/06270 | 10/1987 |
| WO | WO 88/10315 | 12/1988 |
| WO | WO 89/01050 | 2/1989 |
| WO | WO 89/09282 | 10/1989 |
| WO | WO 91/06678 | 5/1991 |
| WO | WO 92/10587 | 6/1992 |
| WO | WO 93/03151 | 2/1993 |
| WO | WO 93/04199 | 3/1993 |
| WO | WO 94/02634 | 2/1994 |
| WO | WO 95/33073 | 12/1995 |
| WO | WO 96/04404 | 2/1996 |
| WO | WO 96/32504 | 10/1996 |
| WO | WO 97/19193 | 5/1997 |
| WO | WO 98/36094 | 8/1998 |
| WO | WO 98/44151 | 10/1998 |
| WO | WO 98/44152 | 10/1998 |
| WO | WO 98/45474 | 10/1998 |
| WO | WO 00/41524 | 7/2000 |
| WO | WO 00/75374 | 12/2000 |

OTHER PUBLICATIONS

Beattie et al., "Hybridization of DNA targets to glass-tethered oligonucleotide probes", *Molecular Biotechnology*, 1995, 4:213-225.

Blanchard et al., "Oligonucleotide array synthesis using ink jets", *Genome Science and Technology*, 1996, 1(3):225.

Chee et al., "Accessing genetic information with high-density DNA arrays", *Science*, 2001, 274(5287):610-4.

Chrisey et al., "Covalent attachment of synthetic DNA to self-assembled monolayerfilms", *Nucleic Acids Research*, 1996, 24(15):3031-3039.

Chu et al., "Derivitization of unprotected polynucleotides", *Nucleic Acids Research*, 1983, 11(18):6514-6529.

Egan et al., "Structural studies and chemistry of bacterial polysaccharides. Invesigations of Phosphodiester-Linked Capsular Polysaccharides Isolated from Haemophilus influenzae Types a, b, c, and f: NMR Spectroscopic Identification and Chemical Modification of End", Groups and the Nature of Base-Catalyzed Hydrolytic Depolymerization, *J. Am. Chem. Soc.*, 1982, 104:2898-2910.

Fodor, "Light-Directed, Spatially Addressable Parallel Chemical Synthesis", *Science*, 1991, 251:767-773.

Fu et al., "Sequencing Double-stranded DNA by Strand Displacement", *Nucleic Acids Research*, 1997, 25(3): 677-679.

Ghosh et al., "Covalent attachment of oligonucleotides to solid supports", *Nucleic Acids Research*, 1987, 15(13):5353-5371.

Gilham, "The synthesis of Celluloses covalently bound nucleotides, polynucleotides, and nucleic acids", *Biochemistry*, 1968, 7(8):2810-2813.

Gingeras et al., "Hybridization properties of immobilized nucleic acids", *Nucleic Acids Research*, 1987, 15:5373-5390.

Guo, Zhen et al., "Direct fluorescence analysis of genetic polymorphisms by hybridization with oligonucleotide arrays on glass supports", *Nucleic Acids Research*, 1994, 22(24):5456-5465.

Joos et al., "Covalent attachment of hybridizable oligonucleotides to glass supports", Analytical Biochemistry, 1997, 247:96-101.

Kremsky et al., "Immobilization of DNA oligonucelotides containing an aldehyde or carboxylic acid group at the 5' terminus", *Nucleic Acids Research*, 1987, 15(7):2891-2909.

Ledbetter et al., "Tissue distribution of ryanodine receptor isoforms and alleles determined by reverse transcription polymerase chain reaction", *The Journal of Biological Chemistry*, 1994, 269:31544-31551.

Lizardi, "Mutation detection and single-molecule counting using isothermal rolling-circle amplification", *Nature Genetics*, 1998, 19:225-232.

Lockhart, D J. et al., "Expression monitoring by hybridization to high-density oligonucleotide arrays", *Nature Biotechnology*, Dec. 1996, ISSN 1087-015., 14 : 1675-1680.

Ludecke et al., "Cloning defined regions of the human genome by microdissection of banded chromosomes and enzymatic amplification", *Nature*, 1989, 338:348-350.

Lund et al., "Assessment of methods for covalent binding of nucleic acids to magnetic beads, Dynabeads, and the characteristics of the bound nucleic acids in hybridization reactions", *Nucleic Acids Research*, 1988, 16(22):10860-10881.

Notomi et al., "Loop-mediated isothermal amplification of DNA", *Nucleic Acids Research*, 2000, 28:i-vii.

Ochman et al., "Genetic applications of an Inverse Polymerase Chain Reaction", *Genetics*, 1988, 120:621-623.

O'Donnell-Maloney et al., "The development of microfabricated array for DNA sequencing and analysis", *Tibtech*, 1996, 14:401-407.

Oroskar et al., "Detection of immobilized amplicons by ELISA-like techniques", *Clinical Chemistry*, 1996, 42:1547-1555.

Peeters et al., "Comparison of four biofunctional reagents for coupling peptides to proteins and the effect of the three moities on the immunogenicity of the conjugates", *Journal of Immunological Methods*, 1989, 120 : 133-143.

Rasmussen et al., "Covalent immobilization of DNA onto polystyrene microwells: The molecules are only bound at the e5' end", *Analytical Biochemistry*, 1991, 198 : 138-142.

Saiki et al., "Enzymatic amplification of B-globin genomic sequences and restriction site analysis for diagnosis of sicke cell anemia", *Science*, 1985, 230:1350-1354.

Saunders et al., "PCR amplification of DNA microdissected from a single polytene chromosome band: a comparison with conventional microcloning", *Nucleic Acids Research*, 1989, 17:9027-9037.

Steigerwald et al., "Ligation-mediated PCR Improves the sensitivity of methylation analysis by restriction enzymes and detection of specific DNA Strand breaks", *Nucleic Acids Research*, 1990, 18:1435-1439.

Sterky et al., "Direct sequencing of bacterial artificial chromosomes [bacS] prokaryotic genomes by biotin capture PCR", *Journal of Biotechnology*, 1998, 60:119-129.

Thomas et al., "Affymetrix: Genes on Chips", *Expr. Opino. Ther. Patents*, 1998, 8:503-508.

Triglia et al., "A procedure for in vitro amplification of DNA segments that lie outside the boundaries of know sequences", *Nucleic Acids Research*, 1988, 16:8186.

Vos et al., "AFLP: a new technique for DNA Fingerprinting", *Nucleic Acids Research*, 1995, 23(21):4407-4414.

Walker, "Empirical Aspects of Strand Displacement Amplification", *PCR Methods* Appl, 1993, 3 : 1-6.

Walker et al., "Isothermal in vitro amplification of DNA by a restriction enzyme/DNA polymerase system", *PNAS*, 1992, 89:392-396.

Walker et al., "Multiplex strand displacement amplification (SDA) and detection of DNA sequences from Mycobacterium tuberculosis and other mycobacteria", *Nucleic Acids Research*, 1994, 22:2670-2677.

Westin et al., "Anchored multiplex amplification on a microelectric chip array", *Nature Biotechnology*, 2000, 18:199-204.

Wolf et al., "Rapid hybridization kinetics of DNA attached to submicron latex particles", *Nucleic Acids Research*, 1987, 15:2911-2926.

(56) References Cited

OTHER PUBLICATIONS

Yang et al., "Covalent Immobilization of oligonucleotides on modified glass/silicon surfaces for solid-phase DNA hybridization and amplification", *Chemistry Letters*, 1998, 257-8.
Yershov et al., "DNA analysis and diagnostics on oligonucleotide microchips", *PNAS US*, 1996, 93:4913-4918.

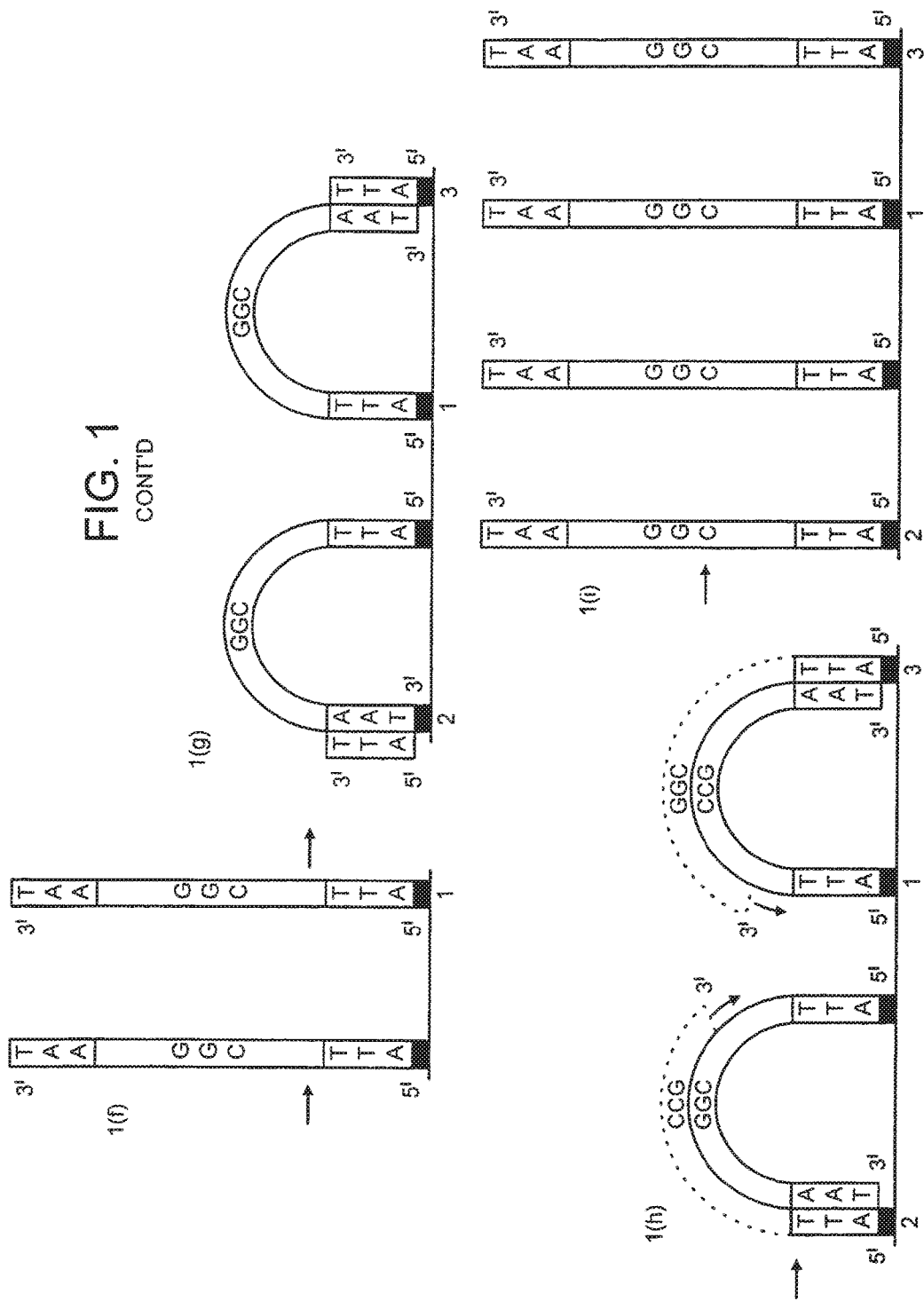

PREPARATION OF TEMPLATES CONTAINING COLONY PRIMER SEQUENCES
(LOCATION OF PRIMERS ON RAGE)

COLONIES FORMED WITH TEMPLATE AND COLONY PRIMER ATTACHED TO THE SUPPORT

SIMULTANEOUS DETECTION OF TWO INDEPENDENT DNA COLONIES

OVERLAY IMAGE OF GREEN AND RED COLONIES

DNA COLONY GENERATION ON GLASS:
EFFECT OF TEMPLATE CONCENTRATION

SEQUENCE LISTING

<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 1
agaaggagaa ggaaagggaa aggg                                              24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 2
caccaaccca aaccaaccca aacc                                              24

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3
gaggccagaa cagttcaagg                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 4
cctgtgacaa gacgactgaa                                                   20

<210> SEQ ID NO 5
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 5

```
tttttttttt caccaaccca aaccaaccca aacc                                       34

<210> SEQ ID NO 6
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 6
tttttttttt agaaggagaa ggaaagggaa aggg                                       34

<210> SEQ ID NO 7
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 7
tttttttttt caccaaccca aaccaaccca aacc                                       34

<210> SEQ ID NO 8
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 8
tttttttttt agaaggagaa ggaaagggaa aggg                                       34

<210> SEQ ID NO 9
<211> LENGTH: 42
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (41)..(42)
<223> OTHER INFORMATION: n is a, c, g, or t

<400> SEQUENCE: 9
agaaggagaa ggaaagggaa agggtttttt tttttttttt nn                              42

<210> SEQ ID NO 10
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 10
agaaggagaa ggaaagggaa aggggg                                                26

<210> SEQ ID NO 11
<211> LENGTH: 52
<212> TYPE: DNA
<213> ORGANISM: Artificial Sequence
<220> FEATURE:
<223> OTHER INFORMATION: Synthetic oligonucleotide primer

<400> SEQUENCE: 11
agaaggagaa ggaaagggaa aggggcggcc gctcgcctgg ttctggaaga ca                   52
```

<210> SEQ ID NO 12
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 12
agaaggagaa ggaaagggaa agggcctgtg acaagacgac tgaa          44

<210> SEQ ID NO 13
<211> LENGTH: 62
<212> TYPE: DNA
<213> ORGANISM: Artificial Sequence
<220> FEATURE:
<223> OTHER INFORMATION: Synthetic oligonucleotide primer

<400> SEQUENCE: 13
tttttttttt agaaggagaa ggaaagggaa aggggcggcc gctgaggcca gtggaagtca          60
ga          62

<210> SEQ ID NO 14
<211> LENGTH: 60
<212> TYPE: DNA
<213> ORGANISM: Artificial Sequence
<220> FEATURE:
<223> OTHER INFORMATION: Synthetic oligonucleotide primer

<400> SEQUENCE: 14
tttttttttt caccaaccca aaccaaccca aaccgagctc aggctgaggc aggagaattg          60

<210> SEQ ID NO 15
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 15
agaaggagaa ggaaagggaa aggggagctg aggaggaaga gagg          44

<210> SEQ ID NO 16
<211> LENGTH: 52
<212> TYPE: DNA
<213> ORGANISM: Artificial Sequence
<220> FEATURE:
<223> OTHER INFORMATION: Synthetic oligonucleotide primer

<400> SEQUENCE: 16
agaaggagaa ggaaagggaa aggggcggcc gctcgcctgg ttctggaaga ca          52

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (11)..(21)
<220> FEATURE:
<221> NAME/KEY: misc_feature
<222> LOCATION: (11)..(11)
<223> OTHER INFORMATION: n is inosine
<220> FEATURE:
<221> NAME/KEY: misc_feature
<222> LOCATION: (13)..(13)

```
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (17)..(17)
<223> OTHER INFORMATION: n is inosine
<220> FEATURE:
<221> NAME/KEY: misc_feature
<222> LOCATION: (19)..(19)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 17
tttttttttt nsnsnsnsns ns                                            22

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 18
cgacagccgg aaggaagagg gagc                                          24

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 19
gagaaggaaa gggaaagg                                                 18

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 20
ggctaggagc tgaggaggaa                                               20
```

METHODS OF NUCLEIC ACID AMPLIFICATION AND SEQUENCING

This invention relates to the field of nucleic acid amplification and sequencing. More specifically, this invention relates to nucleic acid amplification and sequencing methods, and apparatus and kits useful for large scale high throughput amplification and sequencing of nucleic acids.

Nucleic acid sequence analysis has become a corner-stone in many activities in biology, biotechnology and medicine. The ability to determine nucleic acid sequences has become increasingly important as efforts have commenced to determine the sequences of the large genomes of humans and other higher organisms and also, for example, in single nucleotide polymorphism detection and screening and gene expression monitoring. The genetic information provided by nucleic acid sequencing has many applications in areas such as for example drug target discovery and validation, disease diagnosis and risk scoring and organism identification and characterization.

The first step in such applications is the determination of the actual chemical composition of the nucleic acids of interest, more precisely the determination of the sequence of occurrence of the four bases adenine (A), cytosine (C), guanine (G) and thymine (T) or uracil (U) which comprise nucleic acids. However, such applications require the sequencing of nucleic acids on a large scale, making high throughput methods of nucleic acid sequencing extremely desirable.

Methods of nucleic acid sequencing are documented in the art. The two most commonly used are the chemical cleavage technique by Maxam and Gilbert which relies on base-specific chemistry and the now more popular Sanger sequencing technique which relies on an enzymatic chain terminating principle and is now used on a routine basis for nucleic acid sequencing.

In Sanger sequencing, each nucleic acid to be sequenced is replicated in a reaction involving DNA polymerase, deoxynucleotide triphosphates (dNTPs) and dideoxynucleotide triphosphates (ddNTPs). The DNA polymerase can incorporate both dNTPs and ddNTPs into the growing DNA strand. However, once a ddNTP is incorporated, the 3' end of the growing DNA strand lacks a hydroxyl group and is no longer a substrate for chain elongation, thus terminating the nucleic acid chain. Hence, in a particular reaction including one type of ddNTP a mixture of nucleic acids of different lengths is produced, all terminating with the same ddNTP. Usually separate reactions are set up for each of the four types of ddNTP and the distribution of lengths of the nucleic acid fragments produced is analysed by denaturing gel electrophoresis (which resolves nucleic acid fragments according to their size), or more recently, by mass-spectroscopy. Usually, one or more of the deoxynucleotide triphosphates in the reaction mixture is labelled to enable detection of the fragments of different lengths.

The above described methods are disadvantageous because each nucleic acid to be sequenced has to be processed individually during the biochemical reaction. Gel electrophoresis is cumbersome, labour intensive and intrinsically slow even when capillary electrophoresis is used and is not well suited for large scale high throughput sequencing. In addition, the subsequent determination of the sequence is cumbersome. Mass-spectroscopy is still at the prototype level, requires very expensive apparatus and each sample has to be analysed individually.

One way to increase throughput is to process many samples in parallel. Methods using DNA hybridization of nucleic acid probes are in use and allow for some multiplexing of the process during the biochemical and the electrophoretic processes, but at the cost of lengthy additional manipulations.

More recently methods based on DNA chips and DNA hybridization are becoming available (Thomas and Burke Exp. Opin. Ther. Patents 8: 503-508 (1998)). These methods are disadvantageous because for each application, a DNA chip has to be designed and manufactured first: this is a lengthy operation and the price of an individual chip drops only when very large numbers of the chip are required. Also, the chips are not reusable and for each chip only one sample of nucleic acids, e.g. one patient to be diagnosed, can be processed at each time. Finally, the extent of sequence which can be analysed by such a chip is limited to less than 100,000 bases, and is limited to some applications such as DNA genotyping and gene expression profiling.

In most known techniques for nucleic acid sequence analysis, amplification of the nucleic acids of interest is a prerequisite step in order to obtain the nucleic acid in a quantity sufficient for analysis.

Several methods of nucleic acid amplification are well known and documented in the art. For example, nucleic acids can be amplified by inserting the nucleic acid of interest into an expression vector construct. Such vectors can then be introduced into suitable biological host cells and the vector DNA, including the nucleic acid of interest, amplified by culturing the biological host using well established protocols.

Nucleic acids amplified by such methods can be isolated from the host cells by methods well known and documented in the art. However, such methods have the disadvantage of being generally time consuming, labour intensive and difficult to automate.

The technique of DNA amplification by the polymerase chain reaction (PCR) was disclosed in 1985 (Saiki et al. Science 230, 1350-1354) and is now a method well known and documented in the art. A target nucleic acid fragment of interest can be amplified using two short oligonucleotide sequences (usually referred to as primers) which are specific to known sequences flanking the DNA sequence that is to be amplified. The primers hybridize to opposite strands of the double-stranded DNA fragment after it has been denatured, and are oriented so that DNA synthesis by the DNA polymerase proceeds through the region between the two primers, with the primer sequences being extended by the sequential incorporation of nucleotides by the polymerase. The extension reactions create two double-stranded target regions, each of which can again be denatured ready for a second cycle of hybridisation and extension. The third cycle produces two double-stranded molecules that comprise precisely the target region in double-stranded form. By repeated cycles of heat denaturation, primer hybridisation, and extension, there follows a rapid exponential accumulation of the specific target fragment of DNA. Traditionally, this method is performed in solution and the amplified target nucleic acid fragment purified from solution by methods well known in the art, for example by gel electrophoresis.

More recently, however, methods have been disclosed which use one primer grafted to a surface in conjunction with free primers in solution. These methods allow the simultaneous amplification and attachment of a PCR product onto the surface (Oroskar, A. A. et al., *Clinical Chemistry* 42:1547 (1996)).

WO96/04404 (Mosaic Technologies, Inc. et al) discloses a method of detection of a target nucleic acid in a sample which potentially contains the target nucleic acid. The method involves the induction of a PCR based amplification of the target nucleic acid only when the target nucleic acid is present in the sample being tested. For the amplification of the target sequence, both primers are attached to a solid support, which results in the amplified target nucleic acid sequences also being attached to the solid support. The amplification technique disclosed in this document is sometimes referred to as the "bridge amplification" technique. In this technique the two primers are, as for conventional PCR, specifically designed so that they flank the particular target DNA sequence to be amplified. Thus, if the particular target nucleic acid is present in the sample, the target nucleic acid can hybridise to the primers and be amplified by PCR. The first step in this PCR amplification process is the hybridisation of the target nucleic acid to the first specific primer attached to the support ("primer 1"). A first amplification product, which is complementary to the target nucleic acid, is then formed by extension of the primer 1 sequence. On subjecting the support to denaturation conditions the target nucleic acid is released and can then participate in further hybridisation reactions with other primer 1 sequences which may be attached to the support. The first amplification product which is attached to the support, may then hybridise with the second specific primer ("primer 2") attached to the support and a second amplification product comprising a nucleic acid sequence complementary to the first amplification product can be formed by extension of the primer 2 sequence and is also attached to the support. Thus, the target nucleic acid and the first and second amplification products are capable of participating in a plurality of hybridisation and extension processes, limited only by the initial presence of the target nucleic acid and the number of primer 1 and primer 2 sequences initially present and the result is a number of copies of the target sequence attached to the surface.

Since, on carrying out this process, amplification products are only formed if the target nucleic acid is present, monitoring the support for the presence or absence of one or more amplification products is indicative of the presence or absence of a specific target sequence.

The Mosaic technique can be used to achieve an amount of multiplexing in that several different target nucleic acid sequences can be amplified simultaneously by arraying different sets of first and second primers, specific for each different target nucleic acid sequence, on different regions of the solid support.

The disadvantage of the Mosaic process is that, as the first and second primer sequences have to be specific for each target nucleic acid to be amplified, it can only be used to amplify known sequences. In addition, the throughput is limited by the number of different sets of specific primers and subsequently amplified target nucleic acid molecules which can be arrayed in distinct regions of a given solid support and the time taken to array the nucleic acids in distinct regions. Also, the Mosaic process requires that 2 different primers are homogeneously attached by the 5' end to the support within the distinct region where the amplification product is formed. This cannot be achieved with presently available DNA chip manufacturing technology and has to be achieved by some means of sample dispensing. Thus, the density that can be achieved by this approach has the same limitation as other classical arraying technologies. A further limitation is the speed of monitoring the individual distinct regions of the support for the presence or absence of the amplified target nucleic acids.

Arraying of DNA samples is classically performed on membranes (e.g., nylon or nitro-cellulose membranes). The use of suitable robotics (e.g., Q-bot™, Genetix Ltd, Dorset BH23 3TG UK) means that it is possible to obtain a density of up to 10 samples/mm$^2$. In such methods, the DNA is covalently linked to a membrane by physicochemical means (e.g., UV irradiation) and the arraying of large DNA molecules (e.g. molecules over 100 nucleotides long) as well as smaller DNA molecules such as oligonucleotide primers is possible.

Other techniques are known whereby higher density arrays of oligonucleotides can be obtained. For example, approaches based on pre-arrayed glass slides wherein arrays of reactive areas are obtained by ink-jet technology (Blanchard, A. P. and L. Hood, *Microbial and Comparative Genomics*, 1:225 (1996)) or arrays of reactive polyacrylamide gels (Yershov, G. et al., *Proceedings of the National Academy of Science, USA*, 93:4913-4918 (1996)) allow in theory the arraying of up to 100 samples/mm$^2$.

Higher sample densities still are achievable by the use of DNA chips (Fodor, S. P. A. et al., *Science* 251:767(1991)). Currently, chips with 625 oligonucleotide probes/mm$^2$ are used in molecular biology techniques (Lockhart, D. J. et al., *Nature Biotechnology* 14:1675 (1996)). Probe densities of up to 250 000 samples/cm$^2$ (2500/mm$^2$) are claimed to be achievable (Chee, M. et al., *Science* 274:610 (1996)). However, at present up to 132000 different oligonucleotides can be arrayed on a single chips of approximately 2.5 cm$^2$. Importantly, these chips are manufactured in such a way so that the 3'OH end of the oligonucleotide is attached to the solid surface. This means that oligonucleotides attached to chips in such a way cannot be used as primers in a PCR amplification reaction.

Importantly, when PCR products are linked to the vessel in which PCR amplification takes place, the density of the resultant array of PCR products is limited by the available vessel. Currently available vessels are only in 96 well microtiter plate format. These allow only around 0.02 samples of PCR products/mm$^2$ of surface to be obtained.

For example, using the commercially available Nucleolink™ system (Nunc A/S, Roskilde, Denmark) it is possible to achieve simultaneous amplification and arraying of samples at a density of 0.02 samples/mm$^2$ in wells on the surface of which oligonucleotide primers have been grafted. However, technical problems mean that it is unlikely that a significant increase in this sample density will be achieved with this approach.

Thus, it can be seen that in order to increase throughput there is a need in the art for new methods of nucleic acid amplification which allow the simultaneous amplification and array of nucleic acid samples at a higher density, and furthermore, allows the monitoring of samples at a faster rate, preferably in parallel.

In addition, it is apparent that there is a need in the art for new methods of sequencing which allow large numbers of samples to be processed and sequenced in parallel, i.e. there is a need for methods of sequencing which allow significant multiplexing of the process. Significant multiplexing of the sequencing process would in turn lead to a higher throughput than that achievable with the methods of sequencing known in the art. Such new methods would be even more desirable if they could achieve such high throughput sequencing at a reasonable cost and with less labour intensiveness than conventional sequencing techniques.

The present invention describes new methods of solid-phase nucleic acid amplification which enable a large number of distinct nucleic acid sequences to be arrayed and amplified simultaneously and at a high density. The invention also describes methods by which a large number of distinct amplified nucleic acid sequences can be monitored at a fast rate and, if desired, in parallel. The invention also describes methods by which the sequences of a large number of distinct nucleic acids can be determined simultaneously and within a short period of time. The methods are particularly useful in, but not limited to, the sequencing of a whole genome, or situations where many genes (e.g. 500) from many individuals (e.g. 500) have to be sequenced simultaneously, or the simultaneous scoring of large numbers (e.g. millions) of polymorphisms, or the monitoring of the expression of a large number of genes (e.g. 100,000) simultaneously.

The present invention therefore provides a method for amplification of at least one nucleic acid comprising the following steps:—

(1) forming at least one nucleic acid template comprising the nucleic acid(s) to be amplified, wherein said nucleic acid(s) contains at the 5' end an oligonucleotide sequence Y and at the 3' end an oligonucleotide sequence Z and, in addition, the nucleic acid(s) carry at the 5' end a means for attaching the nucleic acid(s) to a solid support;

(2) mixing said nucleic acid template(s) with one or more colony primers X, which can hybridize to the oligonucleotide sequence Z and carries at the 5' end a means for attaching the colony primers to a solid support, in the presence of a solid support so that the 5' ends of both the nucleic acid template and the colony primers bind to the solid support;

(3) performing one or more nucleic acid amplification reactions on the bound template(s), so that nucleic acid colonies are generated.

In a further embodiment of the invention, two different colony primers X are mixed with the nucleic acid template(s) in step (2) of the method. Preferably the sequences of colony primers X are such that the oligonucleotide sequence Z can hybridise to one of the colony primers X and the oligonucleotide sequence Y is the same as one of the colony primers X.

In an alternative embodiment of the invention, the oligonucleotide sequence Z is complementary to oligonucleotide sequence Y, referred to as Y' and colony primer X is of the same sequence as oligonucleotide sequence Y.

In a yet further embodiment of the invention, the colony primer X may comprise a degenerate primer sequence and the nucleic acid template(s) comprise the nucleic acid(s) to be amplified and do not contain oligonucleotide sequences Y or Z at the 5' and 3' ends respectively.

In a further aspect of the invention, the method comprises the additional step of performing at least one step of sequence determination of one or more of the nucleic acid colonies generated in step (3).

Thus the invention also provides a method for sequencing of at least one nucleic acid comprising the following steps:—

(1) forming at least one nucleic acid template comprising the nucleic acid(s) to be sequenced, wherein said nucleic acid(s) contains at the 5' end an oligonucleotide sequence Y and at the 3' end an oligonucleotide sequence Z and, in addition, the nucleic acid(s) carry at the 5' end a means for attaching the nucleic acid(s) to a solid support;

(2) mixing said nucleic acid template(s) with one or more colony primers X, which can hybridize to the oligonucleotide sequence Z and carries at the 5' end a means for attaching the colony primers to a solid support, in the presence of a solid support so that the 5' ends of both the nucleic acid template and the colony primers bind to the solid support;

(3) performing one or more nucleic acid amplification reactions on the bound template(s), so that nucleic acid colonies are generated; and (4) performing at least one step of sequence determination of at least one of the nucleic acid colonies generated.

In a further embodiment of the invention the 5' ends of both the nucleic acid template(s) and the colony primers carry a means for attaching the nucleic acid sequences covalently to the solid support. Preferably this means for covalent attachment is a chemically modifiable functional group, such as for example, a phosphate group, a carboxylic or aldehyde moiety, a thiol, a hydroxyl, a dimethoxyltrityl (DMT), or an amino group, preferably an amino group.

Nucleic acids which may be amplified according to the methods of the invention include DNA, for example, genomic DNA, cDNA, recombinant DNA or any form of synthetic or modified DNA, RNA, mRNA or any form of synthetic or modified RNA. Said nucleic acids may vary in length and may be fragments or smaller parts of larger nucleic acid molecules. Preferably the nucleic acid to be amplified is at least 50 base pairs in length and more preferably 150 to 4000 base pairs in length. The nucleic acid to be amplified may have a known or unknown sequence and may be in a single or double-stranded form. The nucleic acid to be amplified may be derived from any source.

"Nucleic acid template" as used herein refers to an entity which comprises the nucleic acid to be amplified or sequenced in a single-stranded form. As outlined below the nucleic acid to be amplified or sequenced can also be provided in a double stranded form. Thus, "nucleic acid templates" of the invention may be single or double stranded nucleic acids. The nucleic acid templates to be used in the method of the invention can be of variable lengths. Preferably they are at least 50 base pairs in length and more preferably 150 to 4000 base pairs in length. The nucleotides making up the nucleic acid templates may be naturally occurring or non-naturally occurring nucleotides. The nucleic acid templates of the invention not only comprise the nucleic acid to be amplified but may in addition contain at the 5' and 3' end short oligonucleotide sequences. The oligonucleotide sequence contained at the 5' end is referred to herein as Y. Oligonucleotide sequence Y is of a known sequence and can be of variable length. Oligonucleotide sequence Y for use in the methods of the present invention is preferably at least five nucleotides in length, preferably between 5 and 100 nucleotides in length and more preferably of approximately 20 nucleotides in length. Naturally occurring or non-naturally occurring nucleotides may be present in the oligonucleotide sequence Y. As indicated above, preferably the sequence of oligonucleotide Y is the same as the sequence of colony primer X. The oligonucleotide sequence contained at the 3' end of the nucleic acid templates of the invention is referred to herein as Z. Oligonucleotide sequence Z is of a known sequence and can be of variable length. Oligonucleotide sequence Z for use in the methods of the present invention is preferably at least five nucleotides in length, preferably between 5 and 100 nucleotides in length and more preferably of approximately 20 nucleotides in length. Naturally occurring or non-naturally occurring nucleotides may be present in the oligonucleotide sequence Z. Oligonucleotide sequence Z is designed so that it hybridises with one of the colony primers X and preferably is designed so that it is complementary to oligonucleotide sequence Y, referred to herein as Y'. The oligonucleotide sequences Y and Z contained at the 5' and 3' ends respectively of a nucleic acid template need not be located at the extreme ends of the template. For example although the oligonucleotide sequences Y and Z are preferably located at or near the 5' and 3' ends (or termini) respectively of the nucleic acid templates (for example within 0 to 100 nucleotides of the 5' and 3' termini) they may be located further away (e.g. greater than 100 nucleotides) from the 5' or 3' termini of the nucleic acid template. The oligonucleotide sequences Y and Z may therefore be located at any position within the nucleic acid template providing the sequences Y and Z are on either side, i.e. flank, the nucleic acid sequence which is to be amplified.

"Nucleic acid template" as used herein also includes an entity which comprises the nucleic acid to be amplified or sequenced in a double-stranded form. When the nucleic acid template is in a double-stranded form, the oligonucleotide sequences Y and Z are contained at the 5' and 3' ends respectively of one of the strands. The other strand, due to the base pairing rules of DNA, is complementary to the strand containing oligonucleotide sequences Y and Z and thus contains an oligonucleotide sequence Z' at the 5' end and an oligonucleotide sequence Y' at the 3' end.

"Colony primer" as used herein refers to an entity which comprises an oligonucleotide sequence which is capable of hybridizing to a complementary sequence and initiate a specific polymerase reaction. The sequence comprising the colony primer is chosen such that it has maximal hybridising activity with its complementary sequence and very low non-specific hybridising activity to any other sequence. The sequence to be used as a colony primer can include any sequence, but preferably includes 5'-AGAAGGA-GAAGGAAAGGGAAAGGG (SEQ ID NO:1) or 5'CAC-CAACCCAAACCAACCCAAACC (SEQ ID NO:2). The colony primer can be 5 to 100 bases in length, but preferably 15 to 25 bases in length. Naturally occurring or non-naturally occurring nucleotides may be present in the primer. One or two different colony primers may be used to generate nucleic acid colonies in the methods of the present invention. The colony primers for use in the present invention may also include degenerate primer sequences.

"Degenerate primer sequences" as used herein refers to a short oligonucleotide sequence which is capable of hybridizing to any nucleic acid fragment independent of the sequence of said nucleic acid fragment. Such degenerate primers thus do not require the presence of oligonucleotide sequences Y or Z in the nucleic acid template(s) for hybridization to the template to occur, although the use of degenerate primers to hybridise to a template containing the oligonucleotide sequences X or Y is not excluded. Clearly however, for use in the amplification methods of the present invention, the degenerate primers must hybridise to nucleic acid sequences in the template at sites either side, or flanking, the nucleic acid sequence which is to be amplified.

"Solid support" as used herein refers to any solid surface to which nucleic acids can be covalently attached, such as for example latex beads, dextran beads, polystyrene, polypropylene surface, polyacrylamide gel, gold surfaces, glass surfaces and silicon wafers. Preferably the solid support is a glass surface.

"Means for attaching nucleic acids to a solid support" as used herein refers to any chemical or non-chemical attachment method including chemically-modifiable functional groups. "Attachment" relates to immobilization of nucleic acid on solid supports by either a covalent attachment or via irreversible passive adsorption or via affinity between molecules (for example, immobilization on an avidin-coated surface by biotinylated molecules). The attachment must be of sufficient strength that it cannot be removed by washing with water or aqueous buffer under DNA-denaturing conditions.

"Chemically-modifiable functional group" as used herein refers to a group such as for example, a phosphate group, a carboxylic or aldehyde moiety, a thiol, or an amino group.

"Nucleic acid colony" as used herein refers to a discrete area comprising multiple copies of a nucleic acid strand. Multiple copies of the complementary strand to the nucleic acid strand may also be present in the same colony. The multiple copies of the nucleic acid strands making up the colonies are generally immobilised on a solid support and may be in a single or double stranded form. The nucleic acid colonies of the invention can be generated in different sizes and densities depending on the conditions used. The size of colonies is preferably from 0.2 µm to 6 µm, more preferably from 0.3 µm to 4 µm. The density of nucleic acid colonies for use in the method of the invention is typically 10,000/$mm^2$ to 100,000/$mm^2$. It is believed that higher densities, for example, 100,000/$mm^2$ to 1,000,000/$mm^2$ and 1,000,000/$mm^2$ to 10,000,000/$mm^2$ may be achieved.

The methods of the invention can be used to generate nucleic acid colonies. Thus, a further aspect of the invention provides one or more nucleic acid colonies. A nucleic acid colony of the invention may be generated from a single immobilised nucleic acid template of the invention. The method of the invention allows the simultaneous production of a number of such nucleic acid colonies, each of which may contain different immobilised nucleic acid strands.

Thus, a yet further aspect of the invention provides a plurality of nucleic acid templates comprising the nucleic acids to be amplified, wherein said nucleic acids contain at their 5' ends an oligonucleotide sequence Y and at the 3' end an oligonucleotide sequence Z and, in addition, the nucleic acid(s) carry at the 5' end a means for attaching the nucleic acid(s) to a solid support. Preferably this plurality of nucleic acid templates are mixed with a plurality of colony primers X which can hybridize to the oligonucleotide sequence Z and carry at the 5' end a means for attaching the colony primers to a solid support. Preferably said plurality of nucleic acid templates and colony primers are covalently bound to a solid support.

In a further embodiment of the invention, pluralities of two different colony primers X are mixed with the plurality of nucleic acid templates. Preferably the sequences of colony primers X are such that the oligonucleotide sequence Z can hybridise to one of the colony primers X and the oligonucleotide sequence Y is the same as the sequence of one of the colony primers X.

In an alternative embodiment, the oligonucleotide sequence Z is complementary to oligonucleotide sequence Y, (Y') and the plurality of colony primers X are of the same sequence as oligonucleotide sequence Y.

In a yet further embodiment, the plurality of colony primers X may comprise a degenerate primer sequence and the plurality of nucleic acid templates comprise the nucleic acids to be amplified and do not contain oligonucleotide sequences Y or Z at the 5' and 3' ends respectively.

The nucleic acid templates of the invention may be prepared using techniques which are standard or conventional in the art. Generally these will be based on genetic engineering techniques.

The nucleic acids to be amplified can be obtained using methods well known and documented in the art. For example, by obtaining a nucleic acid sample such as, total DNA, genomic DNA, cDNA, total RNA, mRNA etc. by methods well known and documented in the art and generating fragments therefrom by, for example, limited restriction enzyme digestion or by mechanical means.

Typically, the nucleic acid to be amplified is first obtained in double stranded form. When the nucleic acid is provided in single stranded form, for example mRNA, it is first made into a double stranded form by means well known and documented in the art, for example, using oligo-dT primers and reverse transcriptase and DNA polymerase. Once the nucleic acid to be amplified is obtained in double stranded form of appropriate length, oligonucleotide sequences corresponding to the oligonucleotide sequences Y and Z are joined to each end, i.e. to both the 5' and 3' ends of the nucleic acid sequence to form a nucleic acid template. This can be done using methods which are well known and documented in the art, for example by ligation, or by inserting the nucleic acid to be amplified into a biological vector at a site which is flanked by the appropriate oligonucleotide sequences. Alternatively, if at least part of the sequence of the nucleic acid to be amplified is known, the nucleic acid template containing oligonucleotide sequences Y and Z at the 5' and 3' ends respectively, may be generated by PCR using appropriate PCR primers which include sequences specific to the nucleic acid to be amplified. Before attaching the nucleic acid template to the solid support, it can be made into a single stranded form using methods which are well known and documented in the art, for example by heating to approximately 94° C. and quickly cooling to 0° C. on ice.

The oligonucleotide sequence contained at the 5' end of the nucleic acid can be of any sequence and any length and is denoted herein as sequence Y. Suitable lengths and sequences of oligonucleotide can be selected using methods well known and documented in the art. For example the oligonucleotide sequences attached to each end of the nucleic acid to be amplified are normally relatively short nucleotide sequences of between 5 and 100 nucleotides in length. The oligonucleotide sequence contained at the 3' end of the nucleic acid can be of any sequence and any length and is denoted herein as sequence Z. Suitable lengths and sequences of oligonucleotide can be selected using methods well known and documented in the art. For example the oligonucleotide sequences contained at each end of the nucleic acid to be amplified are normally relatively short nucleotide sequences of between 5 and 100 nucleotides in length.

The sequence of the oligonucleotide sequence Z is such that it can hybridise to one of the colony primers X. Preferably, the sequence of the oligonucleotide sequence Y is such that it is the same as one of the colony primers X. More preferably, the oligonucleotide sequence Z is complementary to oligonucleotide sequence Y (Y') and the colony primers X are of the same sequence as oligonucleotide sequence Y.

The oligonucleotide sequences Y and Z of the invention may be prepared using techniques which are standard or conventional in the art, or may be purchased from commercial sources.

When producing the nucleic acid templates of the invention additional desirable sequences can be introduced by methods well known and documented in the art. Such additional sequences include, for example, restriction enzyme sites or certain nucleic acid tags to enable amplification products of a given nucleic acid template sequence to be identified. Other desirable sequences include fold-back DNA sequences (which form hairpin loops or other secondary structures when rendered single-stranded), 'control' DNA sequences which direct protein/DNA interactions, such as for example a promoter DNA sequence which is recognised by a nucleic acid polymerase or an operator DNA sequence which is recognised by a DNA-binding protein.

If there are a plurality of nucleic acid sequences to be amplified then the attachment of oligonucleotides Y and Z can be carried out in the same or different reaction.

Once a nucleic acid template has been prepared, it may be amplified before being used in the methods of the present invention. Such amplification may be carried out using methods well known and documented in the art, for example by inserting the template nucleic acid into an expression vector and amplifying it in a suitable biological host, or amplifying it by PCR. This amplification step is not however essential, as the method of the invention allows multiple copies of the nucleic acid template to be produced in a nucleic acid colony generated from a single copy of the nucleic acid template.

Preferably the 5' end of the nucleic acid template prepared as described above is modified to carry a means for attaching the nucleic acid templates covalently to a solid support. Such a means can be, for example, a chemically modifiable functional group, such as, for example a phosphate group, a carboxylic or aldehyde moiety, a thiol, or an amino group. Most preferably, the thiol, phosphate or amino group is used for 5'-modification of the nucleic acid.

The colony primers of the invention may be prepared using techniques which are standard or conventional in the art. Generally, the colony primers of the invention will be synthetic oligonucleotides generated by methods well known and documented in the art or may be purchased from commercial sources.

According to the method of the invention one or two different colony primers X, can be used to amplify any nucleic acid sequence. This contrasts with and has an advantage over many of the amplification methods known in the art such as, for example, that disclosed in WO 96/04404, where different specific primers must be designed for each particular nucleic acid sequence to be amplified.

Preferably the 5' ends of colony primers X of the invention are modified to carry a means for attaching the colony primers covalently to the solid support. Preferably this means for covalent attachment is a chemically modifiable functional group as described above. If desired, the colony primers can be designed to include additional desired sequences such as, for example, restriction endonuclease sites or other types of cleavage sites each as ribozyme cleavage sites. Other desirable sequences include fold-back DNA sequences (which form hairpin loops or other secondary structures when rendered single-stranded), 'control' DNA sequences which direct a protein/DNA interaction, such as for example a promoter DNA sequence which is recognised by a nucleic acid polymerase or an operator DNA sequence which is recognised by a DNA-binding protein.

Immobilisation of a colony primer X to a support by the 5' end leaves its 3' end remote from the support such that the colony primer is available for chain extension by a polymerase once hybridisation with a complementary oligonucleotide sequence contained at the 3' end of the nucleic acid template has taken place.

Once both the nucleic acid templates and colony primers of the invention have been synthesised they are mixed together in appropriate proportions so that when they are attached to the solid support an appropriate density of attached nucleic acid templates and colony primers is obtained. Preferably the proportion of colony primers in the mixture is higher than the proportion of nucleic acid templates. Preferably the ratio of colony primers to nucleic acid templates is such that when the colony primers and nucleic acid templates are immobilised to the solid support a "lawn" of colony primers is formed comprising a plurality of colony primers being located at an approximately uniform density over the whole or a defined area of the solid support, with one or more nucleic acid templates being immobilised individually at intervals within the lawn of colony primers.

The nucleic acid templates may be provided in single stranded form. However, they may also be provided totally or partly in double stranded form, either with one 5' end or both 5' ends modified so as to allow attachment to the support. In that case, after completion of the attachment process, one might want to separate strands by means known in the art, e.g. by heating to 94° C., before washing the released strands away. It will be appreciated that in the case where both strands of the double stranded molecules have reacted with the surface and are both attached, the result will be the same as in the case when only one strand is attached and one amplification step has been performed. In other words, in the case where both strands of a double stranded template nucleic acid have been attached, both strands are necessarily attached close to each other and are indistinguishable from the result of attaching only one strand and performing one amplification step. Thus, single stranded and double stranded template nucleic acids might be used for providing template nucleic acids attached to the surface and suitable for colony generation.

The distance between the individual colony primers and the individual nucleic acid templates (and hence the density of the colony primers and nucleic acid templates) can be controlled by altering the concentration of colony primers and nucleic acid templates that are immobilised to the support. A preferred density of colony primers is at least 1 fmol/mm$^2$, preferably at least 10 fmol/mm$^2$, more preferably between 30 to 60 fmol/mm$^2$. The density of nucleic acid templates for use in the method of the invention is typically 10,000/mm$^2$ to 100,000/mm$^2$. It is believed that higher densities, for example, 100,000/mm$^2$ to 1,000,000/mm$^2$ and 1,000,000/mm$^2$ to 10,000,000/mm$^2$ may be achieved.

Controlling the density of attached nucleic acid templates and colony primers in turn allows the final density of nucleic acid colonies on the surface of the support to be controlled. This is due to the fact that according to the method of the invention, one nucleic acid colony can result from the attachment of one nucleic acid template, providing the colony primers of the invention are present in a suitable location on the solid support (see in more detail below). The density of nucleic acid molecules within a single colony can also be controlled by controlling the density of attached colony primers.

Once the colony primers and nucleic acid templates of the invention have been immobilised on the solid support at the appropriate density, nucleic acid colonies of the invention can then be generated by carrying out an appropriate number of cycles of amplification on the covalently bound template nucleic acid so that each colony comprises multiple copies of the original immobilised nucleic acid template and its complementary sequence. One cycle of amplification consists of the steps of hybridisation, extension and denaturation and these steps are generally performed using reagents and conditions well known in the art for PCR.

A typical amplification reaction comprises subjecting the solid support and attached nucleic acid template and colony primers to conditions which induce primer hybridisation, for example subjecting them to a temperature of around 65° C. Under these conditions the oligonucleotide sequence Z at the 3' end of the nucleic acid template will hybridise to the immobilised colony primer X and in the presence of conditions and reagents to support primer extension, for example a temperature of around 72° C., the presence of a nucleic acid polymerase, for example, a DNA dependent DNA polymerase or a reverse transcriptase molecule (i.e. an RNA dependent DNA polymerase), or an RNA polymerase, plus a supply of nucleoside triphosphate molecules or any other nucleotide precursors, for example modified nucleoside triphosphate molecules, the colony primer will be extended by the addition of nucleotides complementary to the template nucleic acid sequence.

Examples of nucleic acid polymerases which can be used in the present invention are DNA polymerase (Klenow fragment, T4 DNA polymerase), heat-stable DNA polymerases from a variety of thermostable bacteria (such as Taq, VENT, Pfu, Tfl DNA polymerases) as well as their genetically modified derivatives (TaqGold, VENTexo, Pfu exo). A combination of RNA polymerase and reverse transcriptase can also be used to generate the amplification of a DNA colony. Preferably the nucleic acid polymerase used for colony primer extension is stable under PCR reaction conditions, i.e. repeated cycles of heating and cooling, and is stable at the denaturation temperature used, usually approximately 94° C. Preferably the DNA polymerase used is Taq DNA polymerase.

Preferably the nucleoside triphosphate molecules used are deoxyribonucleotide triphosphates, for example dATP, dTTP, dCTP, dGTP, or are ribonucleoside triphosphates for example dATP, dUTP, dCTP, dGTP. The nucleoside triphosphate molecules may be naturally or non-naturally occurring.

After the hybridisation and extension steps, on subjecting the support and attached nucleic acids to denaturation conditions two immobilised nucleic acids will be present, the first being the initial immobilised nucleic acid template and the second being a nucleic acid complementary thereto, extending from one of the immobilised colony primers X. Both the original immobilised nucleic acid template and the immobilised extended colony primer formed are then able to initiate further rounds of amplification on subjecting the support to further cycles of hybridisation, extension and denaturation. Such further rounds of amplification will result in a nucleic acid colony comprising multiple immobilised copies of the template nucleic acid and its complementary sequence.

The initial immobilisation of the template nucleic acid means that the template nucleic acid can only hybridise with colony primers located at a distance within the total length of the template nucleic acid. Thus the boundary of the nucleic acid colony formed is limited to a relatively local area to the area in which the initial template nucleic acid was immobilised. Clearly, once more copies of the template molecule and its complement have been synthesised by carrying out further rounds of amplification, ie. further rounds of hybridisation, extension and denaturation, then the boundary of the nucleic acid colony being generated will be able to be extended further, although the boundary of the colony formed is still limited to a relatively local area to the area in which the initial nucleic acid template was immobilised.

A schematic representation of a method of nucleic acid colony generation according to an embodiment of the present invention is shown in FIG. 1. FIG. 1(a) shows a colony primer X of the invention (shown here as having the sequence ATT), and a nucleic acid template of the invention containing at the 5' end an oligonucleotide sequence Y, here shown as ATT and at the 3' end an oligonucleotide sequence Z, here shown as AAT, which can hybridise to the colony primer sequence X. In the schematic representation the colony primer X and the oligonucleotide sequences Y and Z are shown as being of only three nucleotides in length. In practice however, it will be appreciated that longer sequences would normally be used. The 5' ends of both the colony primer and the nucleic acid template carry a means for attaching the nucleic acid to a solid support. This means is denoted in FIG. 1 as a black square. This means of attaching may result in a covalent or a non-covalent attachment.

Only one colony primer X and one template nucleic acid are shown in FIG. 1(a) for simplicity. However, in practice a plurality of colony primers X will be present with a plurality of nucleic acid templates. The plurality of colony primers X may comprise two different colony primers X. However, for simplicity the schematic representation shown in FIG. 1 shows only one type of colony primer X, with the sequence ATT. The plurality of nucleic acid templates may comprise different nucleic acid sequences in the central portion between the oligonucleotides Y and Z, but contain the same oligonucleotide sequences Y and Z at the 5' and 3' ends respectively. Only one species of nucleic acid template' is shown for simplicity in FIG. 1, in which a portion of the sequence in the central portion is shown as CGG.

In the presence of a solid support, the 5' ends of both the nucleic acid template and colony primer bind to the support. This is depicted in FIG. 1(b). The support and the attached nucleic acid template and colony primers are then subjected to conditions which induce primer hybridisation. FIG. 1(c) shows a nucleic acid template that has hybridised to a colony primer. Such hybridisation is enabled by virtue of the fact that the oligonucleotide sequence Z at the 3' end of the nucleic acid template can hybridise to the colony primer. In the schematic representation oligonucleotide sequence Z is shown to be complementary to the colony primer, although in practice an exact complementary sequence is not essential, providing hybridisation can occur under the conditions the nucleic acid templates and colony primers are subjected to.

FIG. 1(d) shows the stage of primer extension. Here, under appropriate conditions of temperature and in the presence of a DNA polymerase and a supply of nucleotide precursors, for example dATP, dTTP, dCTP and dGTP, the DNA polymerase extends the colony primer from its 3' end using the nucleic acid template as a template. When primer extension is complete, see FIG. 1(e), it can be seen that a second immobilised nucleic acid strand has been generated which is complementary to the initial nucleic acid template. On separating the two nucleic acid strands by, for example heating, two immobilised nucleic acids will be present, the first being the initial immobilised nucleic acid template and the second being a nucleic acid complementary thereto, extending from one of the immobilised colony primers X, see FIG. 1(f).

Both the original immobilised nucleic acid template and the immobilised extended colony primer formed are then able to hybridise to other colony primers present (depicted as colony primers 2 and 3 in FIG. 1(g)) and after a further round of primer extension (FIG. 1(h)) and strand separation (FIG. 1(i)), four single stranded immobilised strands are provided. Two of these contain sequences corresponding to the original nucleic acid template and two contain sequences complementary thereto.

Further rounds of amplification beyond those shown in FIG. 1 can be carried out to result in a nucleic acid colony comprising multiple immobilised copies of the template nucleic acid and its complementary sequence.

It can thus be seen that the method of the present invention allows the generation of a nucleic acid colony from a single immobilised nucleic acid template and that the size of these colonies can be controlled by altering the number of rounds of amplification that the nucleic acid template is subjected to. Thus the number of nucleic acid colonies formed on the surface of the solid support is dependent upon the number of nucleic acid templates which are initially immobilised to the support, providing there is a sufficient number of immobilised colony primers within the locality of each immobilised nucleic acid template. It is for this reason that preferably the solid support to which the colony primers and nucleic acid templates have been immobilised comprises a lawn of immobilised colony primers at an appropriate density with nucleic acid templates immobilised at intervals within the lawn of primers.

Such so called "autopatterning" of nucleic acid colonies has an advantage over many methods of the prior art in that a higher density of nucleic acid colonies can be obtained due to the fact that the density can be controlled by regulating the density at which the nucleic acid templates are originally immobilised. Such a method is thus not limited by, for example, having specifically to array specific primers on particular local areas of the support and then initiate colony formation by spotting a particular sample containing nucleic acid template on the same local area of primer. The numbers of colonies that can be arrayed using prior art methods, for example those disclosed in WO96/04404 (Mosaic Technologies, Inc.) is thus limited by the density/spacing at which the specific primer areas can be arrayed in the initial step.

By being able to control the initial density of the nucleic acid templates and hence the density of the nucleic acid colonies resulting from the nucleic acid templates, together with being able to control the size of the nucleic acid colonies formed and in addition the density of the nucleic acid templates within individual colonies, an optimum situation can be reached wherein a high density of individual nucleic acid colonies can be produced on a solid support of a large enough size and containing a large enough number of amplified sequences to enable subsequent analysis or monitoring to be performed on the nucleic acid colonies.

Once nucleic acid colonies have been generated it may be desirable to carry out an additional step such as for example colony visualisation or sequence determination (see later). Colony visualisation might for example be required if it was necessary to screen the colonies generated for the presence or absence of for example the whole or part of a particular nucleic acid fragment. In this case the colony or colonies which contain the particular nucleic acid fragment could be detected by designing a nucleic acid probe which specifically hybridises to the nucleic acid fragment of interest.

Such a nucleic acid probe is preferably labelled with a detectable entity such as a fluorescent group, a biotin containing entity (which can be detected by for example an incubation with streptavidin labelled with a fluorescent group), a radiolabel (which can be incorporated into a nucleic acid probe by methods well known and documented in the art and detected by detecting radioactivity for example by incubation with scintillation fluid), or a dye or other staining agent.

Alternatively, such a nucleic acid probe may be unlabelled and designed to act as a primer for the incorporation of a number of labelled nucleotides with a nucleic acid polymerase. Detection of the incorporated label and thus the nucleic acid colonies can then be carried out.

The nucleic acid colonies of the invention are then prepared for hybridisation. Such preparation involves the treatment of the colonies so that all or part of the nucleic acid templates making up the colonies is present in a single stranded form. This can be achieved for example by heat denaturation of any double stranded DNA in the colonies. Alternatively the colonies may be treated with a restriction endonuclease specific for a double stranded form of a sequence in the template nucleic acid. Thus the endonuclease may be specific for either a sequence contained in the oligonucleotide sequences Y or Z or another sequence present in the template nucleic acid. After digestion the colonies are heated so that double stranded DNA molecules are separated and the colonies are washed to remove the non-immobilised strands thus leaving attached single stranded DNA in the colonies.

After preparation of the colonies for hybridisation, the labelled or unlabelled probe is then added to the colonies under conditions appropriate for the hybridisation of the probe with its specific DNA sequence. Such conditions may be determined by a person skilled in the art using known methods and will depend on for example the sequence of the probe.

The probe may then be removed by heat denaturation and, if desired, a probe specific for a second nucleic acid may be hybridised and detected. These steps may be repeated as many times as is desired.

Labelled probes which are hybridised to nucleic acid colonies can then be detected using apparatus including an appropriate detection device. A preferred detection system for fluorescent labels is a charge-coupled device (CCD) camera, which can optionally be coupled to a magnifying device, for example a microscope. Using such technology it is possible to simultaneously monitor many colonies in parallel. For example, using a microscope with a CCD camera and a 10× or 20× objective it is possible to observe colonies over a surface of between 1 $mm^2$ and 4 $mm^2$, which corresponds to monitoring between 10 000 and 200 000 colonies in parallel. Moreover, it is anticipated that this number will increase with improved optics and larger chips.

An alternative method of monitoring the colonies generated is to scan the surface covered with colonies. For example systems in which up to 100 000 000 colonies could be arrayed simultaneously and monitored by taking pictures with the CCD camera over the whole surface can be used. In this way, it can be seen that up to 100 000 000 colonies could be monitored in a short time.

Any other devices allowing detection and preferably quantitation of fluorescence on a surface may be used to monitor the nucleic acid colonies of the invention. For example fluorescent imagers or confocal microscopes could be used.

If the labels are radioactive then a radioactivity detection system would be required.

In methods of the present invention wherein the additional step of performing at least one step of sequence determination of at least one of the nucleic acid colonies generated is performed, said sequence determination may be carried out using any appropriate solid phase sequencing technique. For example, one technique of sequence determination that may be used in the present invention involves hybridising an appropriate primer, sometimes referred to herein as a "sequencing primer", with the nucleic acid template to be sequenced, extending the primer and detecting the nucleotides used to extend the primer. Preferably the nucleic acid used to extend the primer is detected before a further nucleotide is added to the growing nucleic acid chain, thus allowing base by base in situ nucleic acid sequencing.

The detection of incorporated nucleotides is facilitated by including one or more labelled nucleotides in the primer extension reaction. Any appropriate detectable label may be used, for example a fluorophore, radiolabel etc. Preferably a fluorescent label is used. The same or different labels may be used for each different type of nucleotide. Where the label is a fluorophore and the same labels are used for each different type of nucleotide, each nucleotide incorporation can provide a cumulative increase in signal detected at a particular wavelength. If different labels are used then these signals may be detected at different appropriate wavelengths. If desired a mixture of labelled and unlabelled nucleotides are provided.

In order to allow the hybridisation of an appropriate sequencing primer to the nucleic acid template to be sequenced the nucleic acid template should normally be in a single stranded form. If the nucleic acid templates making up the nucleic acid colonies are present in a double stranded form these can be processed to provide single stranded nucleic acid templates using methods well known in the art, for example by denaturation, cleavage etc.

The sequencing primers which are hybridised to the nucleic acid template and used for primer extension are preferably short oligonucleotides, for example of 15 to 25 nucleotides in length. The sequence of the primers is designed so that they hybridise to part of the nucleic acid template to be sequenced, preferably under stringent conditions. The sequence of the primers used for sequencing may have the same or similar sequences to that of the colony primers used to generate the nucleic acid colonies of the invention. The sequencing primers may be provided in solution or in an immobilised form.

Once the sequencing primer has been annealed to the nucleic acid template to be sequenced by subjecting the nucleic acid template and sequencing primer to appropriate conditions, determined by methods well known in the art, primer extension is carried out, for example using a nucleic acid polymerase and a supply of nucleotides, at least some of which are provided in a labelled form, and conditions suitable for primer extension if a suitable nucleotide is provided. Examples of nucleic acid polymerases and nucleotides which may be used are described above.

Preferably after each primer extension step a washing step is included in order to remove unincorporated nucleotides which may interfere with subsequent steps. Once the primer extension step has been carried out the nucleic acid colony is monitored in order to determine whether a labelled nucleotide has been incorporated into an extended primer. The primer extension step may then be repeated in order to determine the next and subsequent nucleotides incorporated into an extended primer.

Any device allowing detection and preferably quantitation of the appropriate label, for example fluorescence or radioactivity, may be used for sequence determination. If the label is fluorescent a CCD camera optionally attached to a magnifying device (as described above), may be used. In fact the devices used for the sequence determining aspects of the present invention may be the same as those described above for monitoring the amplified nucleic acid colonies.

The detection system is preferably used in combination with an analysis system in order to determine the number and nature of the nucleotides incorporated at each colony after each step of primer extension. This analysis, which may be carried out immediately after each primer extension step, or later using recorded data, allows the sequence of the nucleic acid template within a given colony to be determined.

If the sequence being determined is unknown, the nucleotides applied to a given colony are usually applied in a chosen order which is then repeated throughout the analysis, for example dATP, dTTP, dCTP, dGTP. If however, the sequence being determined is known and is being resequenced, for example to analyse whether or not small differences in sequence from the known sequence are present, the sequencing determination process may be made quicker by adding the nucleotides at each step in the appropriate order, chosen according to the known sequence. Differences from the given sequence are thus detected by the lack of incorporation of certain nucleotides at particular stages of primer extension.

Thus it can be seen that full or partial sequences of the amplified nucleic acid templates making up particular nucleic acid colonies may be determined using the methods of the present invention.

In a further embodiment of the present invention, the full or partial sequence of more than one nucleic acid can be determined by determining the full or partial sequence of the amplified nucleic acid templates present in more than one nucleic acid colony. Preferably a plurality of sequences are determined simultaneously.

Carrying out sequence determination of nucleic acids using the method of the present invention has the advantage that it is likely to be very reliable due to the fact that large numbers of each nucleic acid to be sequenced are provided within each nucleic acid colony of the invention. If desired, further improvements in reliability can be obtained by providing a plurality of nucleic acid colonies comprising the same nucleic acid template to be sequenced, then determining the sequence for each of the plurality of colonies and comparing the sequences thus determined.

Preferably the attachment of the colony primer and nucleic acid template to the solid support is thermostable at the temperature to which the support may be subjected to during the nucleic acid amplification reaction, for example temperatures of up to approximately 100° C., for example approximately 94° C. Preferably the attachment is covalent in nature.

In a yet further embodiment of the invention the covalent binding of the colony primers and nucleic acid template(s) to the solid support is induced by a crosslinking agent such as for example 1-ethyl-3-(3-dimethylaminopropyl)-carbodiimide hydrochloride (EDC), succinic anhydride, phenyldiisothiocyanate or maleic anhydride, or a hetero-bifunctional crosslinker such as for example m-maleimidobenzoyl-N-hydroxysuccinimide ester (MBS), N-succinimidyl[4-iodoacethyl] aminobenzoate (SIAB), Succinimidyl 4-[N-maleimidomethyl]cyclohexane-1-carboxylate (SMCC), N-γ-maleimidobutyryloxy-succinimide ester (GMBS), Succinimidyl-4-[p-maleimidophenyl] butyrate (SMPB) and the sulfo (water-soluble) corresponding compounds. The preferred crosslinking reagents for use in the present invention, are s-SIAB, s-MBS and EDC.

In a yet further embodiment of the invention the solid support has a derivatised surface. In a yet further embodiment the derivatised surface of the solid support is subsequently modified with bifunctional crosslinking groups to provide a functionalised surface, preferably with reactive crosslinking groups.

"Derivatised surface" as used herein refers to a surface which has been modified with chemically reactive groups, for example amino, thiol or acrylate groups.

"Functionalised surface" as used herein refers to a derivatised surface which has been modified with specific functional groups, for example the maleic or succinic functional moieties.

In the method of the present invention, to be useful for certain applications, the attachment of colony primers and nucleic acid templates to a solid support has to fulfill several requirements. The ideal attachment should not be affected by either the exposure to high temperatures and the repeated heating/cooling cycles employed during the nucleic acid amplification procedure. Moreover the support should allow the obtaining of a density of attached colony primers of at least 1 fmol/mm$^2$, preferably at least 10 fmol/mm$^2$, more preferably between 30 to 60 fmol/mm$^2$. The ideal support should have a uniformly flat surface with low fluorescence background and should also be thermally stable (non-deformable). Solid supports, which allow the passive adsorption of DNA, as in certain types of plastic and synthetic nitrocellulose membranes, are not suitable. Finally, the solid support should be disposable, thus should not be of a high cost.

For these reasons, although the solid support may be any solid surface to which nucleic acids can be attached, such as for example latex beads, dextran beads, polystyrene, polypropylene surface, polyacrylamide gel, gold surfaces, glass surfaces and silicon wafers, preferably the solid support is a glass surface and the attachment of nucleic acids thereto is a covalent attachment.

The covalent binding of the colony primers and nucleic acid templates to the solid support can be carried out using techniques which are known and documented in the art. For example, epoxysilane-amino covalent linkage of oligonucleotides on solid supports such as porous glass beads has been widely used for solid phase in situ synthesis of oligonucleotides (via a 3'end attachment) and has also been adapted for 5' end oligonucleotide attachment. Oligonucleotides modified at the 5' end with carboxylic or aldehyde moieties have been covalently attached on hydrazine-derivatized latex beads.

Other approaches for the attachment of oligonucleotides to solid surfaces use crosslinkers, such as succinic anhydride, phenyldiisothiocyanate, or maleic anhydride. Another widely used crosslinker is 1-ethyl-3-(3-dimethylamonipropyl)-carbodiimide hydrochloride (EDC). EDC chemistry was first as including attaching DNA templates to paper (cellulose) via the 5' end terminal phosphate group. Using EDC chemistry, other supports have been used such as, latex beads, polystyrene microwells, controlled-pore glass and dextran molecules. The condensation of 5' amino-modified oligonucleotides with carbodiimide mediated reagent have been described for 5' terminal phosphate modification group.

The yield of oligonucleotide attachment via the 5' termini using carbodiimides can reach 60%, but non-specific attachment via the internal nucleotides of the oligonucleotide is a major drawback. Enhancement to 85% the specific attachment via the 5' end by derivatizing the surface using secondary amino groups has been described.

More recent papers have reported the advantages of the hetero-bifunctional cross-linkers. Hetero- or mono-bifunctional cross-linkers have been widely used to prepare peptide carrier conjugate molecules (peptideprotein) in order to enhance immunogenicity in animals. Most of these grafting reagents have been described to form stable covalent links in aqueous solution. These crosslinking reagents have been used to bind DNA onto a solid surface at only one point of the molecule.

The efficiency and stability of DNA solid phase attachment using 6 different hetero-bifunctional cross-linkers has been studied. In this example, the attachment occurs only at the 5' end of DNA oligomers modified by a thiol group. This type of attachment has been described for the attachment of DNA targets in a MALDI-TOF sequence analysis and for determining base sequence of nucleic acid on a solid surface.

Very few studies concerning the thermal stability of the attachment of the oligonucleotides to the solid support have been done. With the Succinimidyl-4-[p-maleimidophenyl] butyrate (SMPB) cross-linker, almost 60% of molecules have been reported to be released from the glass surface during heat treatment. But the thermal stability of the other reagents have not been described.

In order to generate nucleic acid colonies via the solid phase amplification reaction as described in the present application, colony primers and nucleic acid templates need to be specifically attached at their 5' ends to the solid surface, preferably glass. Briefly, the glass surface can be derivatized with reactive amino groups by silanization using aminoalkoxy silanes. Suitable silane reagents include aminopropyltrimethoxy-silane, aminopropyltriethoxysilane and 4-aminobutyltriethoxysilane. Glass surfaces can also be derivatized with other reactive groups, such as acrylate or epoxy using epoxysilane, acrylatesilane and acrylamidesilane. Following the derivatization step, nucleic acid molecules (colony primers or nucleic acid templates) having a chemically modifiable functional group at their 5' end, for example phosphate, thiol or amino groups are covalently attached to the derivatized surface by a crosslinking reagent such as those described above.

Alternatively, the derivatization step can be followed by attaching a bifunctional cross-linking reagent to the surface amino groups thereby providing a modified functionalized surface. Nucleic acid molecules (colony primers or nucleic acid templates) having 5'-phosphate, thiol or amino groups are then reacted with the functionalized surface forming a covalent linkage between the nucleic acid and the glass.

Potential cross-linking and grafting reagents that can be used for covalent DNA/oligonucleotide grafting on the solid support include succinic anhydride, (1-ethyl-3[3-dimethylaminopropyl] carbodiimide hydrochloride (EDC), m-maleimidobenzoyl-N-hydroxysuccinimide ester (MBS), N-succinimidyl[4-iodoacethyl] aminobenzoate (SIAB), Succinimidyl 4-[N-maleimidomethyl]cyclohexane-1-carboxylate (SMCC), N-y-maleimidobutyryloxy-succinimide ester (GMBS), Succinimidyl-4-[p-maleimidophenyl] butyrate (SMPB) and the sulfo (water-soluble) corresponding compounds. The preferred crosslinking reagents, according to the present invention, are s-SIAB, s-MBS and EDC. s-MBS is a maleimide-succinimide hetero-bifunctional cross-linker and s-SIAB is an iodoacetyl-succinimide hetero-bifunctional cross-linker. Both are capable of forming a covalent bond respectively with SH groups and primary amino groups. EDC is a carbodiimide-reagent that mediates covalent attachment of phosphate and amino groups.

The colony primers and nucleic acid templates are generally modified at the 5' end by a phosphate group or by a primary amino group (for EDC grafting reagent) or a thiol group (for s-SIAB or s-MBS linkers).

Thus, a further aspect of the invention provides a solid support, to which there is attached a plurality of colony primers X as described above and at least one nucleic acid template as described above, wherein said nucleic acid templates contain at their 5' ends an oligonucleotide sequence Y as described above, and at their 3' ends an oligonucleotide sequence Z as described above. Preferably a plurality of nucleic acid templates are attached to said solid support, which is preferably glass. Preferably the attachment of the nucleic acid templates and colony primers to the solid support is covalent. By performing one or more rounds of nucleic acid amplification on the immobilised nucleic acid template(s) using methods as described above, nucleic acid colonies of the invention may be formed. A yet further aspect of the invention is, therefore, a support comprising one or more nucleic acid colonies of the invention. A yet further aspect of the invention provides the use of the solid supports of the invention in methods of nucleic acid amplification or sequencing. Such methods of nucleic acid amplification or sequencing include the methods of the present invention.

A yet further aspect of the invention provides the use of a derivatized or functionalized support, prepared as described above in methods of nucleic acid amplification or sequencing. Such methods of nucleic acid amplification or sequencing include the methods of the present invention.

A yet further aspect of the invention provides an apparatus for carrying out the methods of the invention or an apparatus for producing a solid support comprising nucleic acid colonies of the invention. Such apparatus might comprise for example a plurality of nucleic acid templates and colony primers of the invention bound, preferably covalently, to a solid support as outlined above, together with a nucleic acid polymerase, a plurality of nucleotide precursors such as those described above, a proportion of which may be labelled, and a means for controlling temperature. Alternatively, the apparatus might comprise for example a support comprising one or more nucleic acid colonies of the invention. Preferably the apparatus also comprises a detecting means for detecting and distinguishing signals from individual nucleic acid colonies arrayed on the solid support according to the methods of the present invention. For example such a detecting means might comprise a charge-coupled device operatively connected to a magnifying device such as a microscope as described above.

Preferably any apparatuses of the invention are provided in an automated form.

The present application provides a solution to current and emerging needs that scientists and the biotechnology industry are trying to address in the fields of genomics, pharmacogenomics, drug discovery, food characterization and genotyping. Thus the method of the present invention has potential application in for example: nucleic acid sequencing and re-sequencing, diagnostics and screening, gene expression monitoring, genetic diversity profiling, whole genome polymorphism discovery and scoring, the creation of genome slides (whole genome of a patient on a microscope slide) and whole genome sequencing.

Thus the present invention may be used to carry out nucleic acid sequencing and re-sequencing, where for example a selected number of genes are specifically amplified into colonies for complete DNA sequencing. Gene re-sequencing allows the identification of all known or novel genetic polymorphisms of the investigated genes. Applications are in medical diagnosis and genetic identification of living organisms.

For use of the present invention in diagnostics and screening, whole genomes or fractions of genomes may be amplified into colonies for DNA sequencing of known single nucleotide polymorphisms (SNP). SNP identification has application in medical genetic research to identify genetic risk factors associated with diseases. SNP genotyping will also have diagnostic applications in pharmaco-genomics for the identification and treatment of patients with specific medications.

For use of the present invention in genetic diversity profiling, populations of for example organisms or cells or tissues can be identified by the amplification of the sample DNA into colonies, followed by the DNA sequencing of the specific "tags" for each individual genetic entity. In this way, the genetic diversity of the sample can be defined by counting the number of tags from each individual entity.

For use of the present invention in gene expression monitoring, the expressed mRNA molecules of a tissue or organism under investigation are converted into cDNA molecules which are amplified into sets of colonies for DNA sequencing. The frequency of colonies coding for a given mRNA is proportional to the frequency of the mRNA molecules present in the starting tissue. Applications of gene expression monitoring are in bio-medical research.

A whole genome slide, where the entire genome of a living organism is represented in a number of DNA colonies numerous enough to comprise all the sequences of that genome may be prepared using the methods of the invention. The genome slide is the genetic card of any living organism. Genetic cards have applications in medical research and genetic identification of living organisms of industrial value.

The present invention may also be used to carry out whole genome sequencing where the entire genome of a living organism is amplified as sets of colonies for extensive DNA sequencing. Whole genome sequencing allows for example, 1) a precise identification of the genetic strain of any living organism; 2) to discover novel genes encoded within the genome and 3) to discover novel genetic polymorphisms.

The applications of the present invention are not limited to an analysis of nucleic acid samples from a single organism/patient. For example, nucleic acid tags can be incorporated into the nucleic acid templates and amplified, and different nucleic acid tags can be used for each organism/patient. Thus, when the sequence of the amplified nucleic acid is determined, the sequence of the tag may also be determined and the origin of the sample identified.

Thus, a further aspect of the invention provides the use of the methods of the invention, or the nucleic acid colonies of the invention, or the plurality of nucleic acid templates of the invention, or the solid supports of the invention, for providing nucleic acid molecules for sequencing and re-sequencing, gene expression monitoring, genetic diversity profiling, diagnosis, screening, whole genome sequencing, whole genome polymorphism discovery and scoring and the preparation of whole genome slides (ie. the whole genome of an individual on one support), or any other applications involving the amplification of nucleic acids or the sequencing thereof.

A yet further aspect of the invention provides a kit for use in sequencing, re-sequencing, gene expression monitoring, genetic diversity profiling, diagnosis, screening, whole genome sequencing, whole genome polymorphism discovery and scoring, or any other applications involving the amplification of nucleic acids or the sequencing thereof. This kit comprises a plurality of nucleic acid templates and colony primers of the invention bound to a solid support, as outlined above.

The invention will now be described in more detail in the following non-limiting Examples with reference to the following drawings in which:

FIG. 1 (steps a-1): shows a schematic representation of a method of nucleic acid colony generation according to an embodiment of the invention.

Figure 2A:
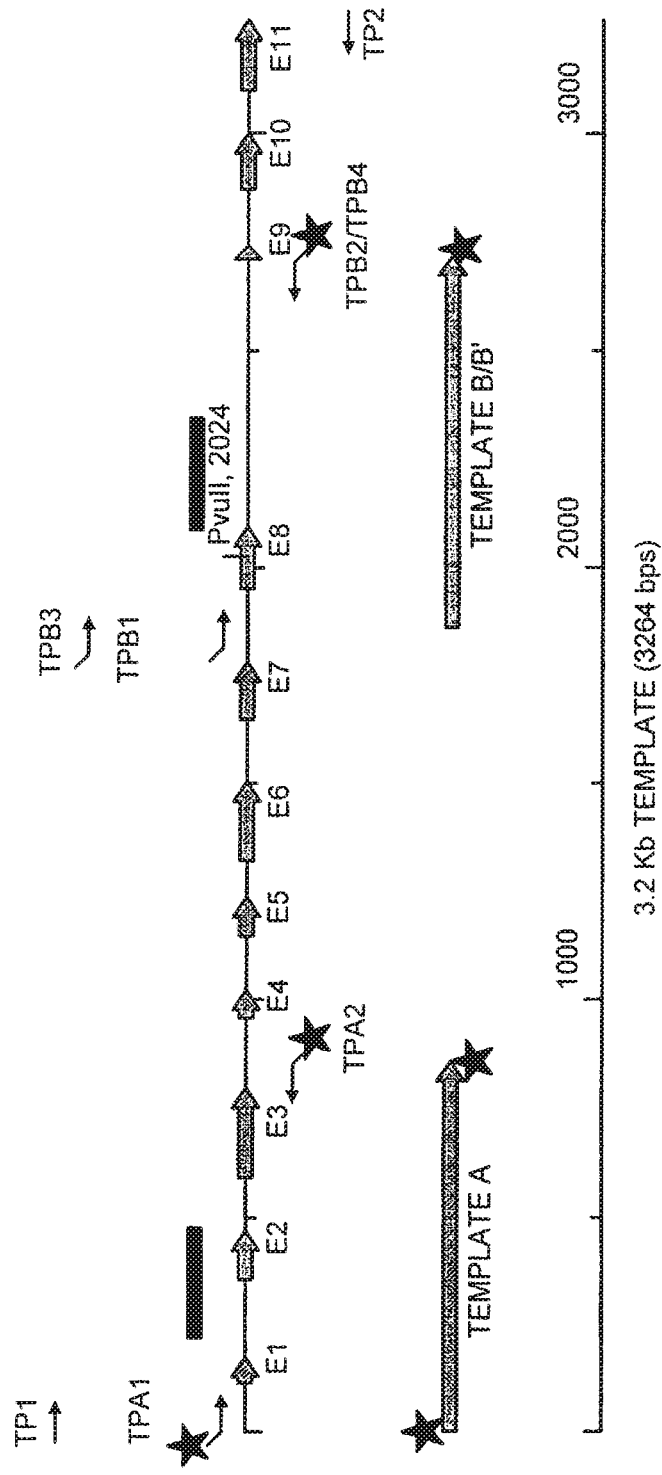

FIG. 2A: Schematic representation of template preparation and subsequent attachment to the solid surface. In FIG. 2a the preparation of Templates A, B and B' containing colony primer sequences is shown. The 3.2 Kb template is generated from genomic DNA using PCR primers TP1 and TP2. Templates A (854 bp) and B (927 bp) are generated using PCR primers TPA1/TPA2 or TPB1/TPB2, respectively. The TPA1 and TPB1 oligonucleotides are modified at their 5'-termini with either a phosphate or thiol group for subsequent chemical attachment (☆). Note that the templates obtained contain sequences corresponding to colony primers CP1 and/or CP2. The 11 exons of the gene are reported as "E1 to E11".

Figure 2B:
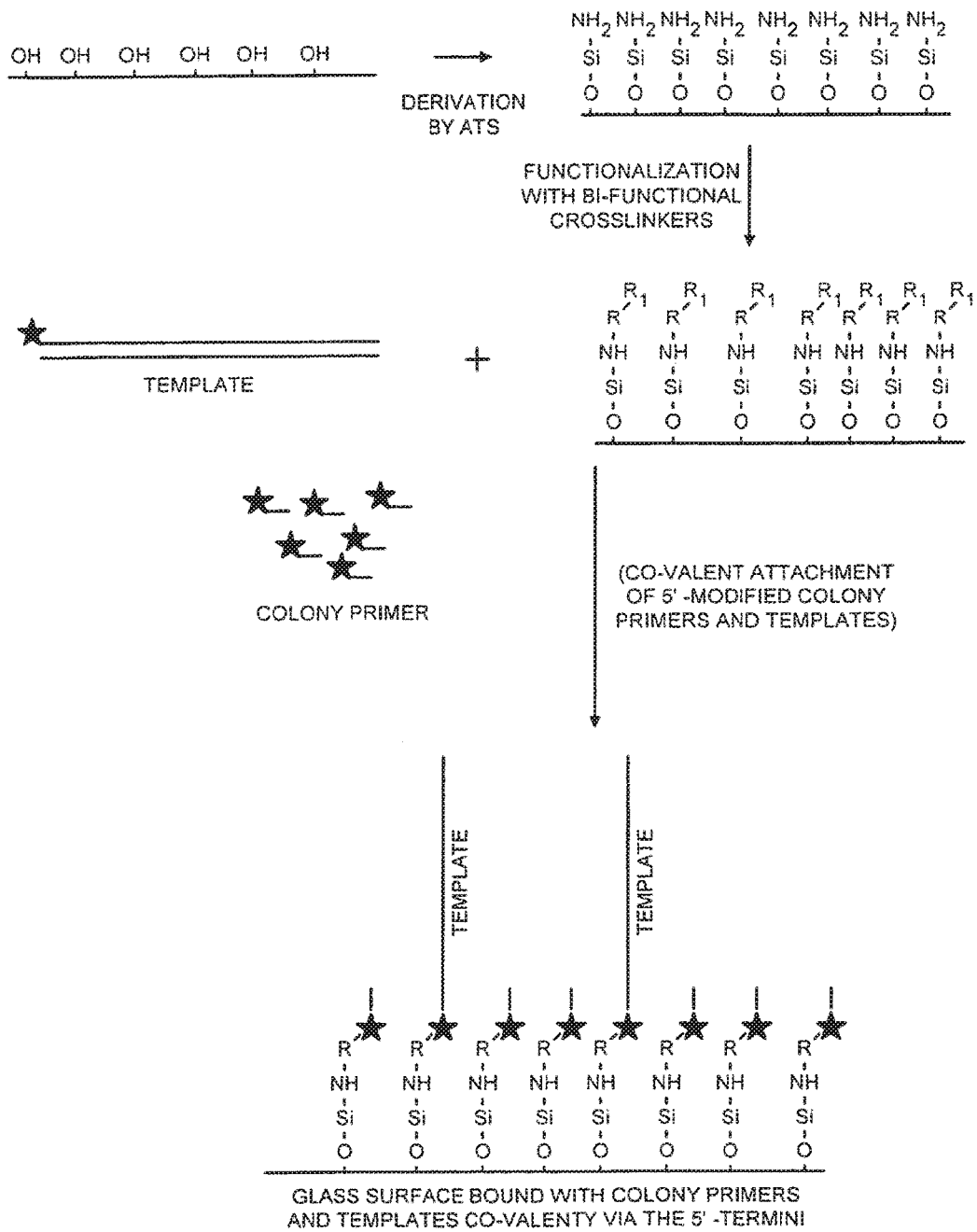

FIG. 2B: In FIG. 2b the chemical attachment of colony primers and templates to glass surface is shown. Derivatization by ATS (aminopropyltriethoxysilane) is exemplified.

Figure 3:
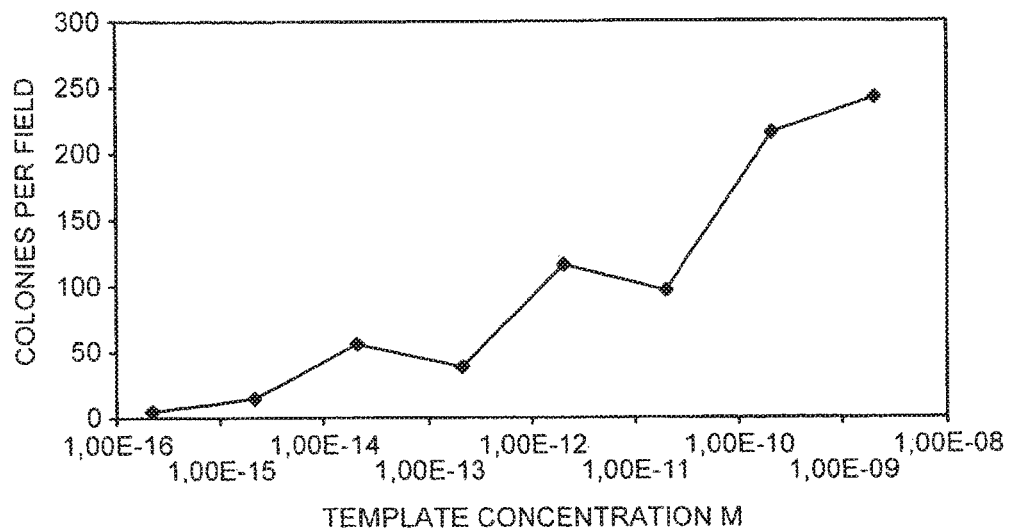

FIG. 3: DNA colonies generated from a colony primer. It shows the number of colonies observed per 20× field as a function of the concentration of template bound to the well. The lowest concentration of detectable template corresponds to $10^{-13}$ M.

Figure 4A:
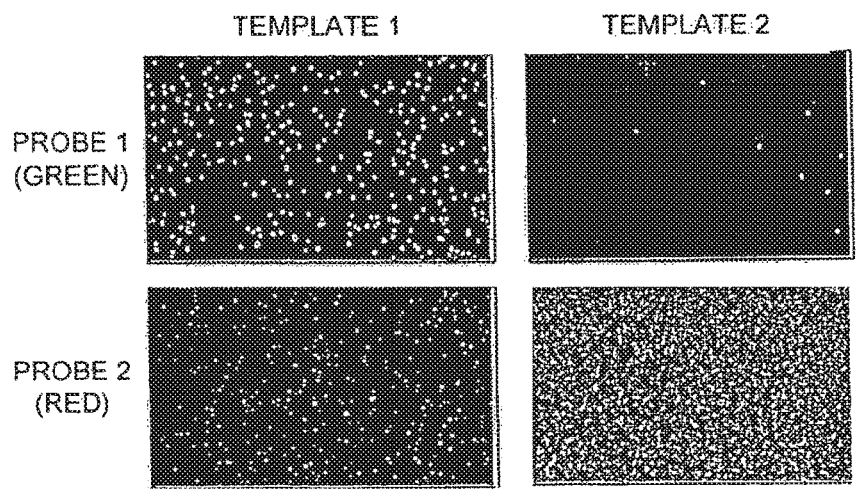

FIG. 4A: Representation of discrimination between colonies originated from two different templates. FIG. 4a shows the images of colonies made from both templates and negative controls. Upper left panel: Template 1, probe 1; Upper right panel: Template 2, probe 2; Lower left panel: Template 1, probe 2; and Lower right panel: Template 2, probe 2.

Figure 4B:
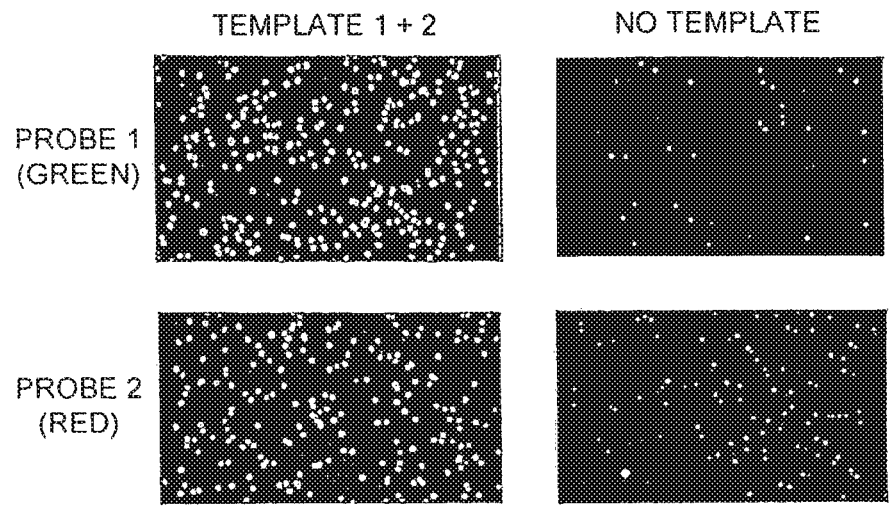

FIG. 4b shows the colonies from both templates at the same position in the same well visualised with two different colours and negative controls. Upper left panel: Template 1+2, probe 1; Upper right panel: No template, probe 2; Lower left panel: Template 1+2, probe 2; and Lower right panel: No Template, probe 2.

Figure 4C:
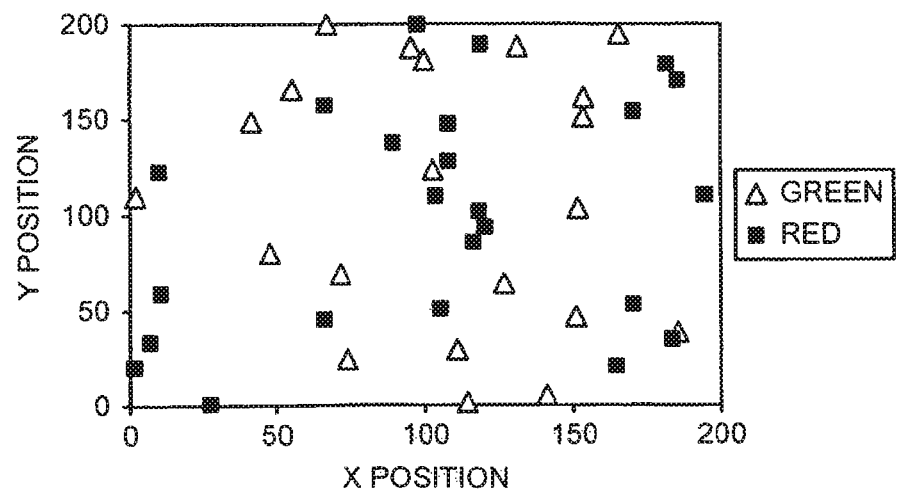

FIG. 4c shows the coordinates of both colony types in a sub-section of a microscopy field. FIG. 4c demonstrates that colonies from different templates do not coincide.

Figure 5:
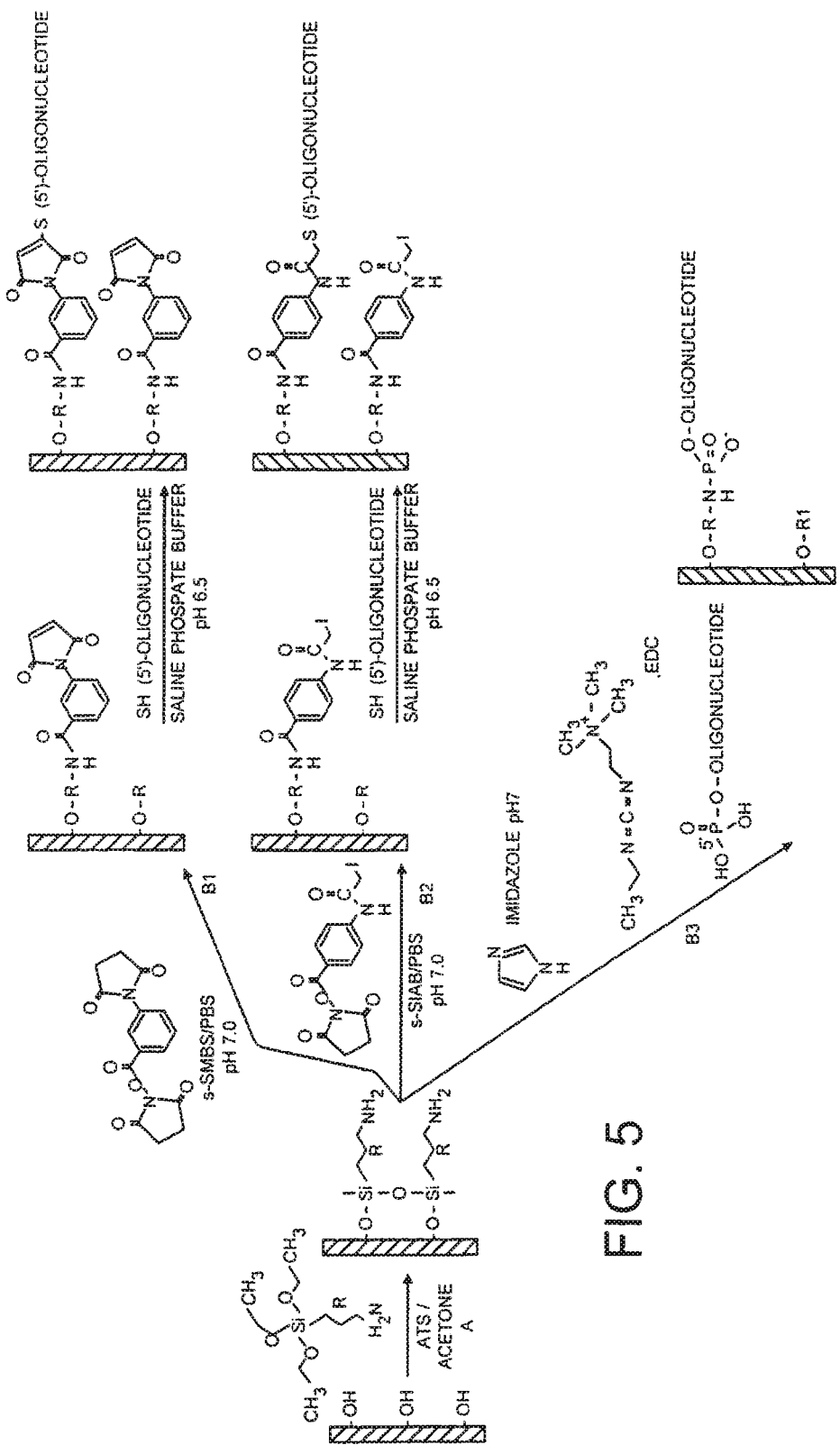

FIG. 5: Reaction schemes of the template or oligonucleotide attachment on glass. Step A is the derivatization of the surface: glass slide are treated with acidic solution to enhance free hydroxyl group on the surface. The pretreated slides are immersed into a solution of aminosilane. ATS: Aminopropyl triethoxysilane. Step B: B1 or B2 is the functionalization of glass surface with cross-linkers followed by oligonucleotide attachment. Amino group reacts with a cross linking agent via an amide bond: step B1; s-MBS (sulfo m-maleimidobenzoyl-N-hydroxy-succinimide ester) step B2; s-SIAB (sulfo N-succinimidyl [4-iodoacethyl] aminobenzoate). The oligonucleotides (5'end thiol modified oligonucleotide) are attached to the surface via formation of a covalent bound between the thiol and the double bond of the maleimide. Phosphate buffered saline: (PBS, 0.1 M NaH2P04, pH: 6.5, 0.15 M NaCl). B3: Attachment of oligonucleotides using EDC and Imidazole. 5'end phosphate of the modified oligonucleotides reacts with imidazole in the presence of EDC to give 5'-phosphor-imidazolide derivatives (not shown). The derivatives form a phosphoramidate bond with amino groups of the derivatized glass surface. EDC: 1-ethyl-3-(3-dimethyl-amonipropyl)-carbodiimide hydrochloride.

Figure 6:
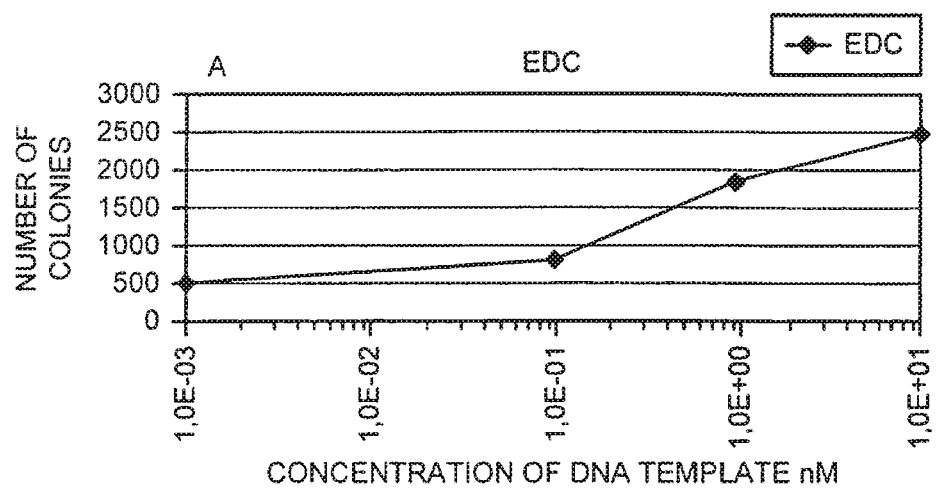
Figure 6:
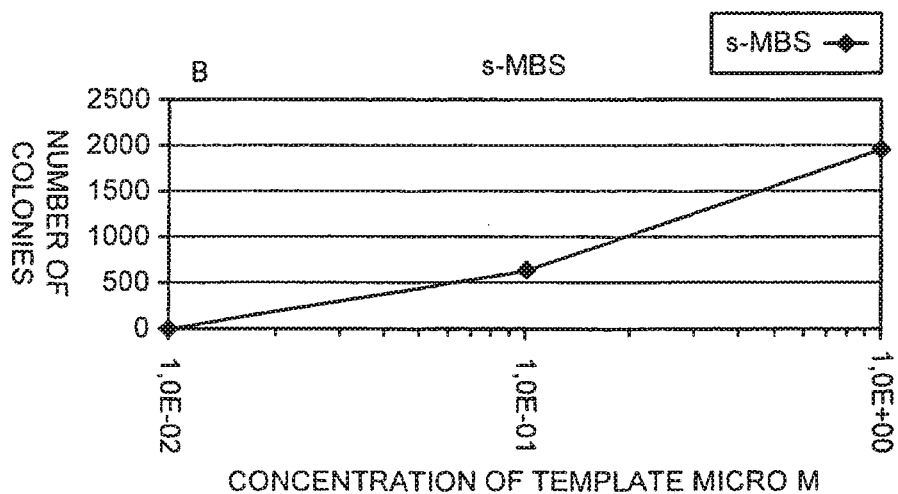

FIG. 6 (Panels A and B): shows the number of colonies observed per 20× field as a function of the concentration of template bound to the well. DNA template were bound at different concentration either via the mediated coupling reagent (EDC) on amino derivatized glass surface (Panel A) or on s-MBS functionalized glass surface (Panel B). Double strand DNA colonies were submitted to restriction enzyme and the recovered single strands hybridized with a complementary oligonucleotide, cy5 fluorescently labeled.

Figure 7:
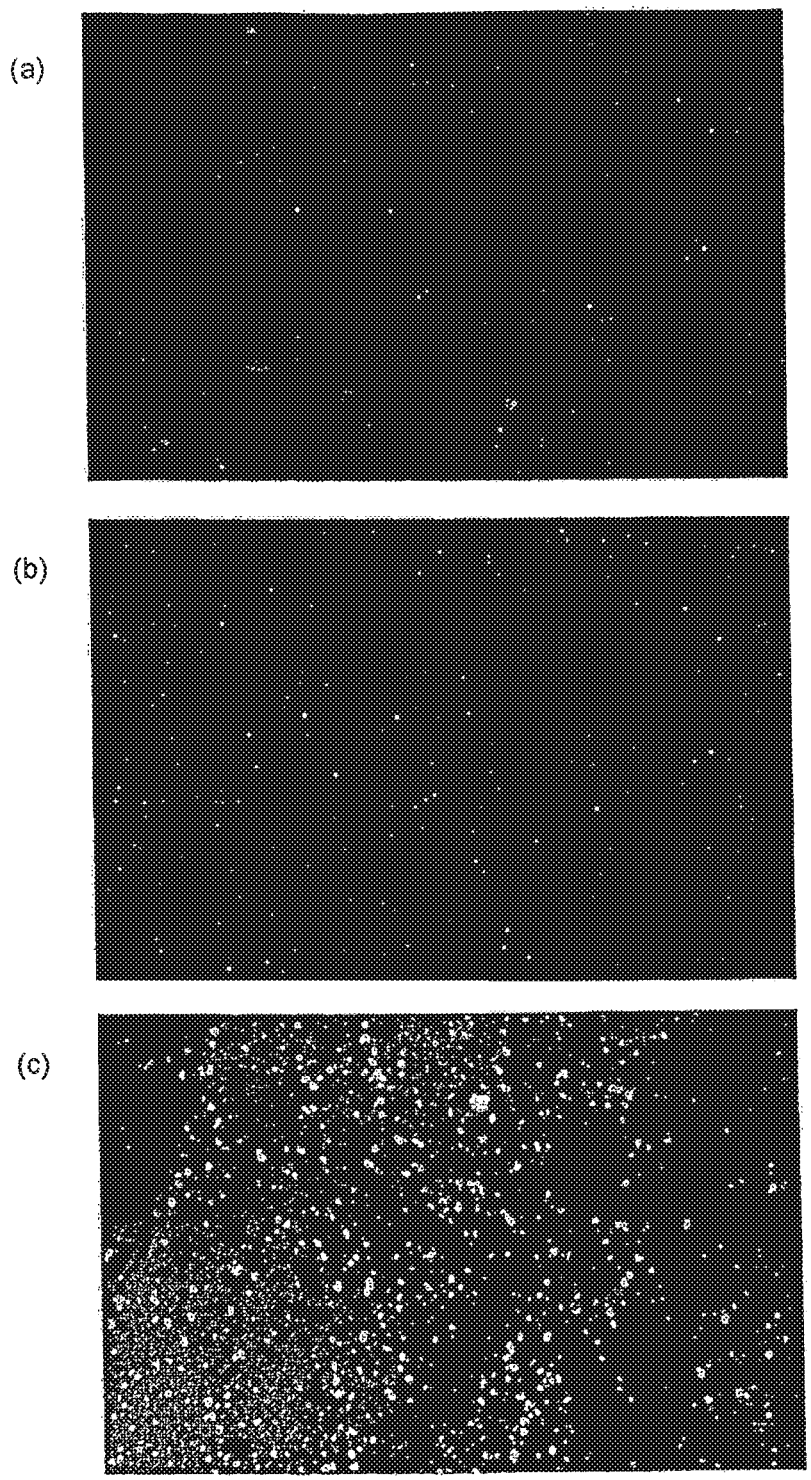

FIG. 7 Panel (a): shows an example of in situ sequencing from DNA colonies generated on glass. FIG. 7 Panel (a) shows the result after incubation with Cy5™-dCTP on a sample that has not been incubated with primer p181. One will appreciate only 5 blurry spots can be observed, indicating that no dramatic spurious effect is taking place (such as Cy5™-dCTP aggregate precipitation, adsorption or simply non specific incorporation to the DNA in the colonies or on the surface).

FIG. 7 Panel (b) shows the result after incubation with Cy5™-dUTP on a sample that has been incubated with primer p181. One will appreciate that no fluorescent spot can be observed, indicating that the incorporation of a fluorescent base cannot take place in detectable amounts when the nucleotide proposed for incorporation does not correspond to the sequence of the template following the hybridized primer.

FIG. 7 Panel (c) shows the result after incubation with Cy5™-dCTP on a sample that has been incubated with primer p181. One will appreciate that many fluorescent spots can be observed, indicating that the incorporation of a fluorescent base can indeed take place in detectable amounts when the nucleotide proposed for incorporation does correspond to the sequence of the template following the hybridized primer.

Figure 8:
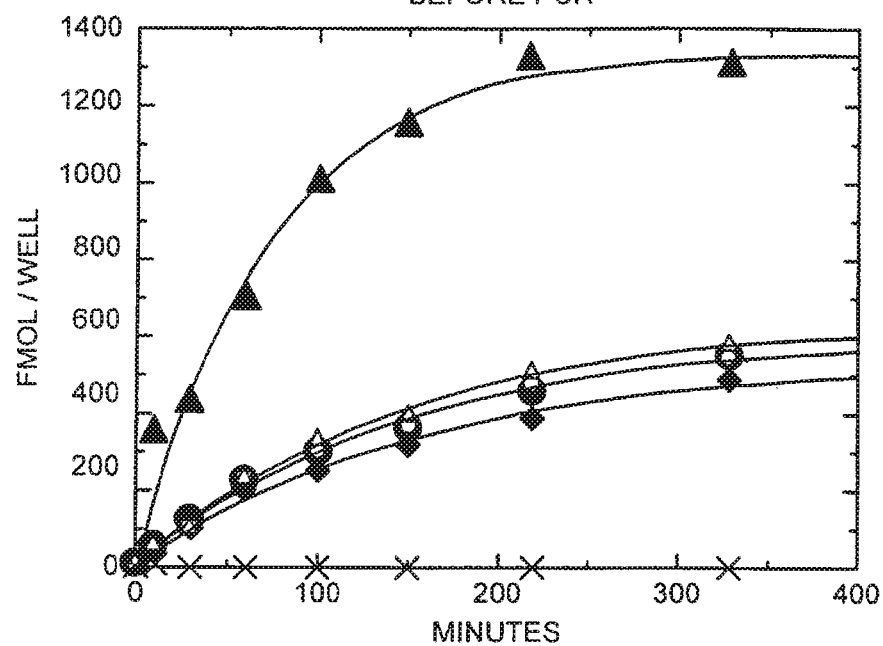
Figure 8:
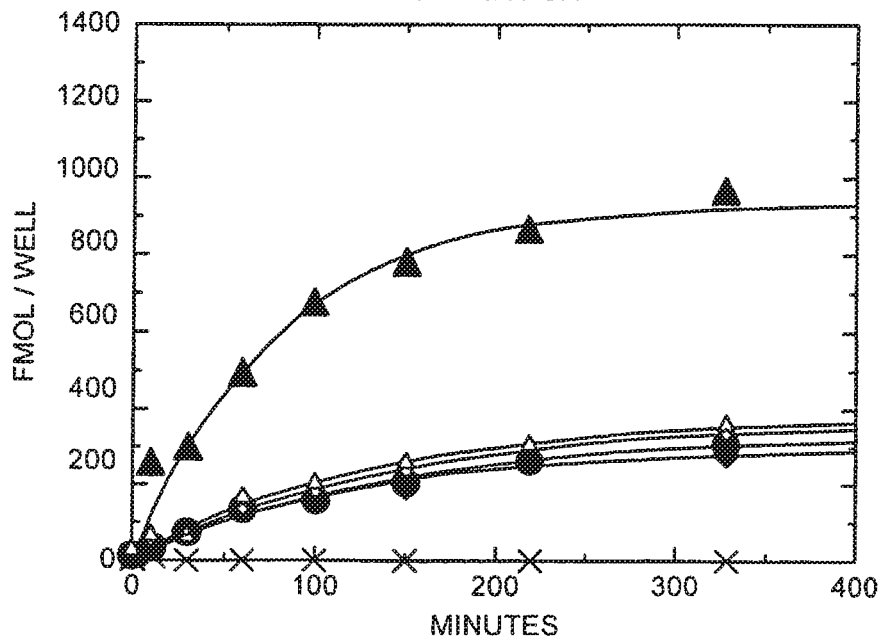

FIG. 8 (Top and Bottom Panels): shows hybridization of probes to oligonucleotides attached to Nucleolink, before (Top Panel) and after (Bottom Panel) PCR cycling. The figure shows R58 hybridization to CP2 (5'-(phosphate)-TTTTTTTTTAGAAGGAGAAGGAAAGGGAAAGGG) (SEQ ID NO:6) closed circles, CP8 (5'(amino-hexamethylene)-TTTTTTTTTAGAAGGA-GAAGGAAAGGGAAAGGG)(SEQ ID NO:6) closed triangles, CP9(5'(hydroxyl)-TTTTTTTTTAGAAGGAGAAGGAAAGGGAAAGGG) (SEQ ID NO:6) diamonds, CP10(5'(dimethoxytrityl)-TTTTTTTTTAGAAGGAGAAGGAAAGGGAAAGGG) (SEQ ID NO:6) open circles and CP11(5'(biotin)-TTTTTTTTTAGAAGGAGAAGGAAAGGGAAAGGG) (SEQ ID NO:6) open triangles.

EXAMPLES

Example 1

Preparation of DNA Templates Suitable for the Generation of DNA Colonies

DNA colonies have been generated from DNA templates and colony primers. The term "colony primer sequence" as used herein refers to a sequence corresponding to the sequence of a colony primer and is elsewhere sometimes referred to as "oligonucleotide sequence Y" or "oligonucleotide sequence Z"'.

The properties of the colony primers have been chosen based on a selection for oligonucleotide primers that show little non-specific nucleotide incorporation in the presence of heat-stable DNA polymerases. The colony primers, CPα (5'-p CACCAACCCAAACCAACCCAAACC) (SEQ ID NO:2) and CPβ (5'-p AGAAGGA-GAAGGAAAGGGAAAGGG) SEQ ID NO:1) have been selected due to their low incorporation of radiolabeled $\alpha^{32}$P-dCTP in the presence of a stable DNA polymerase (AmpliTaq, Perkin Elmer, Foster City, Calif.) in the standard buffer and under thermocycling conditions (94° C. for 30 seconds, 65° C. for 1 minute, 72° C. for 2 minutes, 50 cycles).

A 3.2 Kb DNA fragment was taken as a model system to demonstrate the feasibility of colony generation using colony primers and DNA templates. The chosen template comprises the human gene for the receptor for advanced glycosylation end-products (HUMOXRAGE, GenBank Acc. No. D28769). The RAGE-specific primers are depicted in Table 1. The 3.2 Kb template was generated by PCR amplification from 0.1 µg human genomic DNA with 1 µM primers TP1 and TP2 with 1 unit of DNA polymerase (AmpliTaq, Perkin Elmer, Foster City, Calif.) in the standard buffer and under thermocycling conditions (94° C. for 30 seconds, 65° C. for 1 minute, 72° C. for 5 minutes, 40 cycles). This 3.2 Kb DNA fragment was used as a template for secondary PCR to generate two shorter templates for colony generation (Templates A and B). The primers used to generate the shorter templates contain both sequences specific to the template and sequences of colony primers CP1 and CP2 to amplify the DNA on the solid surface. In general, the PCR primer used to generate a DNA template is modified at the 5'-terminus with either a phosphate or thiol moiety. Thus after the PCR amplification, DNA fragments are generated which contain the colony primer sequences at one or both termini adjoining the RAGE DNA fragment of interest (see FIG. 2a).

Template A (double stranded template containing the colony primer sequence, CPβ at both termini) was generated with 0.1 ng of the 3.2 Kb template with 1 AM primers TPA1 and 1 AM TPA2 with 1 unit of DNA polymerase (AmpliTaq, Perkin Elmer, Foster City, Calif.) in the standard buffer and under thermocycling conditions (94° C. for 30 seconds, 65° C. for 1 minute, 72° C. for 1 minutes, 30 cycles). The products were then purified over Qiagen Qia-quick columns (Qiagen GmbH, Hilden, Germany).

Template B (double stranded template which contains colony primer sequences corresponding to CP(3) was generated with 0.1 ng of the 3.2 Kb template with 1 µM primers TPB1 and 1 µM TPB2 with 1 unit of DNA polymerase (AmpliTaq, Perkin Elmer, Foster City, Calif.) in the standard buffer and under thermocycling conditions (94° C. for 30 seconds, 65° C. for 1 minute, 72° C. for 1 minutes, 30 cycles). The products were then purified over Qiagen Qia-quick columns (Qiagen GmbH, Hilden, Germany).

Template B' (double stranded template containing colony primer sequences corresponding to CPα and CPβ at either end) was generated with 0.1 ng of the 3.2 Kb template with 1 µM primers TPB3 and 1 µM TPB4 with 1 unit of (AmpliTaq, Perkin Elmer, Foster City, Calif.) in the standard buffer and under thermocycling conditions (94° C. for 30 seconds, 65° C. for 1 minute, 72° C. for 1 minutes, 30 cycles). The products were then purified over Qiagen Qia-quick columns (Qiagen GmbH, Hilden, Germany).

All the specific oligonucleotides employed for the DNA templates preparation and for the DNA colony generation have been reported in the Table 1 together with any chemical modification.

A general scheme showing the chemical attachment of colony primers and templates to the glass surface is reported in FIG. 2b, where the derivatization by ATS (aminopropyltriethoxysilane) is reported, as a non-limitative example.

TABLE 1

List of oligonucleotides used for templates preparation and colonies generation:

| Name | SEQ ID NO: | DNA sequence | Coordinates (orientation) | Oligonucleotide Modification | Use |
|---|---|---|---|---|---|
| TP1 | 3 | GAGGCCAGAACAGT TCAAGG | 9810 (R) | | Template 3.2 Kb |
| TP2 | 4 | CCTGTGACAAGACG ACTGAA | 6550 (F) | | Template 3.2 Kb |
| CP1 | 5 | TTTTTTTTTTCACC AACCCAAACCAACC CAAACC | None | 5'P | Generate colonies |
| CP2 | 6 | TTTTTTTTTTAGAA GGAGAAGGAAAGGG AAAGGG | None | 5'P | Generate colonies |
| CP3 | 7 | TTTTTTTTTTCACC AACCCAAACCAACC CAAACC | None | 5'SH | Generate colonies |
| CP4 | 8 | TTTTTTTTTTAGAA GGAGAAGGAAAGGG AAAGGG | None | 5'SH | Generate colonies |
| CP5 | 9 | AGAAGGAGAAGGAA AGGGAAAGGGTTTT TTTTTTTTTTNN | None | 5'P | Generate colonies |
| CP6 | 10 | AGAAGGAGAAGGAA AGGGAAAGGGGG | None | 5'P | Generate colonies |
| CP7 | 5 | TTTTTTTTTTCACC AACCCAAACCAACC CAAACC | None | 5'(NH$_2$) | Generate colonies |
| CP8 | 6 | TTTTTTTTTTAGAA GGAGAAGGAAAGGG AAAGGG | None | 5'(NH$_2$) | Generate colonies |
| CP9 | 6 | TTTTTTTTTTAGAA GGAGAAGGAAAGGG AAAGGG | None | 5'(OH) | Control oligo |
| CP10 | 6 | TTTTTTTTTTAGAA GGAGAAGGAAAGGG AAAGGG | None | 5'(DMT) | Control oligo |
| CP11 | 6 | TTTTTTTTTTAGAA GGAGAAGGAAAGGG AAAGGG | None | 5'(biotin) | Control oligo |
| TPA1 | 12 | AGAAGGAGAAGGAA AGGGAAAGGGCCTG TGACAAGACGACTG AA | 6550 (F) | 5'P | Template A |
| TPA2 | 13 | TTTTTTTTTTAGAA GGAGAAGGAAAGGG AAAGGGGCGGCCGC TGAGGCCAGTGGAA GTCAGA | 7403 (R) | 5'P | Template A |
| TPB3 | 14 | TTTTTTTTTTCACC AACCCAAACCAACC CAAACCGAGCTCAG GCTGAGGCAGGAGA ATTG | 9049 (F) | None | Template B' |
| TPB1 | 15 | AGAAGGAGAAGGAA AGGGAAAGGGGAGC TGAGGAGGAAGAGA GG | 9265 (F) | None | Template B |

TABLE 1-continued

List of oligonucleotides used for templates preparation and colonies generation:

| Name | SEQ ID NO: | DNA sequence | Coordinates (orientation) | Oligonucleotide Modification | Use |
|---|---|---|---|---|---|
| TPB2 | 16 | AGAAGGAGAAGGAA AGGGAAAGGGGCGG CCGCTCGCCTGGTT CTGGAAGACA | 8411 (R) | 5'P | Template B |
| TPB4 | 16 | AGAAGGAGAAGGAA AGGGAAAGGGGCGG CCGCTCGCCTGGTT CTGGAAGACA | 9265 (R) | 5'SH | Template B' |

Coordinate from HUMOXRAGE gene Accession number D28769
(R) means "reverse" and (F) means "forward"

Example 1a

Preparation of a Random DNA Template Flanked by a Degenerate Primer

A 3.2 Kb DNA fragment was taken as a model system to demonstrate the feasibility of colony generation from random primer PCR amplification. This strategy can be applied to sequencing of DNA fragments of approximately 100 Kb in length and, by combination of fragments to whole genomes. A fragment of DNA of 3.2 Kb was generated by PCR from human genomic DNA using PCR primers TP1 5'-pGAGGCCAGAACAGTTCAAGG (SEQ ID NO:3) and TP1 5'-pCCTGTGACAAGACGACTGAA (SEQ ID NO:4), as described in example 1. The 3.2 Kb fragment was cut in smaller fragments by a combination of restriction enzymes (EcoR1 and HhaI yielding 4 fragments of roughly 800 bp). The cut or uncut fragment DNAs were then mixed with the degenerate primer, p252 (5'-P TTTTTTTTTTISISISISISIS (SEQ ID NO:17), where I stands for inosine (which pairs with A, T and C) and S stands for G or C) and covalently coupled to the Nucleolink wells (Nunc, Denmark). The tubes were then subjected to random solid phase PCR amplification and visualized by hybridisation with labeled DNA probes, as will be described in Example 2a.

Example 2

Covalent Binding of DNA Templates and Colony Primers on Solid Support (Plastic) and Colony Formation with a Colony Primer Covalent Binding of Template and Colony Primer to the Solid Support (Plastic)

A colony primer (CP2, 5'-TTTTTTTTTTAGAAGGA-GAAGGAAAGGGAAAGGG) (SEQ ID NO: 6), phosphorylated at its 5' terminus (Microsynth GmBH, Switzerland), was attached onto Nucleolink plastic microtitre wells (Nunc, Denmark) in the presence of varying doses of Template A (prepared as described in example 1). 8 wells were set up in duplicate with seven 1/10 dilutions of template with CP2, starting with the highest concentration of 1 nM.

Microtitre wells, to which CP2 colony primer and the template are covalently bound were prepared as follows. In each Nucleolink well, 30 µl of a 1 µM solution of the colony primer with varying concentrations of template diluted down from 1 nM in 10 mM 1-methyl-imidazole (pH 7.0) (Sigma Chemicals) was added. To each well, 10 µl of 40 mM 1-ethyl-3-{3-dimethylaminopropyl)-carbodiimide (pH 7.0) (Sigma Chemicals) in 10 mM 1-methyl-imidazole, was added to the solution of colony primer and template. The wells were then sealed and incubated at 50° C. overnight. After the incubation, wells were rinsed twice with 200 µl of RS (0.4 N NaOH, 0.25% Tween 20), incubated 15 minutes with 200 µl RS, washed twice with 200 µl RS and twice with 200 µl TNT (100 mM TrisHCl pH 7.5, 150 mM NaCl, 0.1% Tween 20). Tubes were dried at 50° C. and were stored in a sealed plastic bag at 4° C.

Colony Generation

Colony growing was initiated in each well with 20 µl of PCR mix; the four dNTPs (0.2 mM), 0.1% BSA (bovine serum albumin), 0.1% Tween 20, 8% DMSO (dimethylsulfoxide, Fluka, Switzerland), 1×PCR buffer and 0.025 units/µl of AmpliTaq DNA polymerase (Perkin Elmer, Foster City, Calif.). The wells were then placed in the thermocycler and growing was performed by incubating the sealed wells 5 minutes at 94° C. and cycling for 50 repetitions the following conditions: 94° C. for 30 seconds, 65° C. for 2 minutes, 72° C. for 2 minutes. After completion of this program, the wells were kept at 8° C. until further use. Prior to hybridization wells are filled with 50 µL TE (10 mM Tris, 1 mM EDTA, pH 7.4) heated at 94° C. for 5 minutes and chilled on ice before probe addition at 45° C.

Colonies Visualization

Probe: The probe was a DNA fragment of 1405 base pairs comprising the sequence of the template at their 3' end (nucleotide positions 8405 to 9259). The DNA probe was synthesized by PCR using two primers: p47 (5'-GGCTAG-GAGCTGAGGAGGAA), amplifying from base 8405, and TP2, biotinylated at 5' end, amplifying from base 9876 of the antisense strand.

Hybridization and Detection: The probe was diluted to 1 nM in "easyhyb" (Boehringer-Mannheim, Germany) and 20 µL added to each well. The probe and the colonies were denatured at 94° C. for 5 min and then incubated 6 hours at 50° C. Excess probes was washed at 50° C. in 2×SSC with 0.1% Tween. The DNA probes were bound to avidin coated green fluorescence fluorospheres of a diameter of 0.04µ (Molecular Probes) in TNT for 1 hour at room temperature. Excess beads were washed with TNT. Colonies were visualized by microscopy and image analysis as described in example 2a. FIG. 3 shows the number of colonies observed per 20× field as a function of the concentration of template bound to the well. The lowest concentration of detectable template corresponds to $10^{-13}$ M.

Example 2a

Covalent Binding of DNA Templates and Colony Primers on Solid Support (Plastic) and Colony Formation with a Degenerate Primer Covalent Binding of Template and Colony Primer to the Solid Support (Plastic)

Microtitre wells with p252 and template DNA fragments were prepared as follows:

In each Nucleolink well, 30 µl of a 1 µM solution of the colony primer p252 with varying concentrations of template diluted down from 0.5 nM in 10 mM 1-methyl-imidazole (pH 7.0) (Sigma Chemicals) was added. To each well, 10 µl of 40 mM 1-ethyl-3-(3-dimethylamino-propyl)-carbodiimide (pH 7.0) (Sigma Chemicals) in 10 mM 1-methyl-imidazole, was added to the solution of colony primer and template. The wells were then sealed and incubated at 50° C. overnight. After the incubation, wells were rinsed twice with 200 µl of RS (0.4N NaOH, 0.25% Tween 20), incubated 15 minutes with 200 µl RS, washed twice with 200 µl RS and twice with 200 µl TNT (100 mM TrisHCl pH7.5, 150 mM NaCl, 0.1% Tween 20). Tubes were dried at 50° C. and were stored in a sealed plastic bag at 4° C.

Colony Generation

DNA colony generation was performed with a modified protocol to allow random priming in each well with 20 µl of PCR mix; the four dNTPs (0.2 mM each), 0.1% BSA, 0.1% Tween 20, 8% DMSO (dimethylsulfoxide, Fluka, Switzerland), 1×PCR buffer and 0.025 units/µl of AmpliTaq DNA polymerase (Perkin Elmer, Foster City, Calif.). The wells were then placed in the thermocycler and amplification was performed by incubating the sealed wells 5 minutes at 94° C. and cycling for 50 repetitions the following conditions: 94° C. for 30 seconds, 65° C. for 2 minutes, 72° C. for 2 minutes. After completion of this program, the wells were kept at 8° C. until further use. Prior to hybridization wells are filled with 50 µL TE (10 mM Tris 1 mM EDTA pH 7.4) heated at 94° C. for 5 minutes and chilled on ice before probe addition at 45° C.

Colonies Visualization

Probes: Two DNA fragments of 546 and 1405 base pairs comprising the sequences of either extremities of the original template were amplified by PCR. The antisense strand of the probe was labeled with biotin, through the use of a 5'-biotinylated PCR primer. The base pair coordinates of the probes were 6550 to 7113 and 6734 to 9805.

Hybridization and detection: The probes were diluted to 1 nM in "easyhyb" (Boehringer-Mannheim, Germany) and 20 µL added to each well. The probe and the colonies were denatured at 94° C. for 5 min and then incubated 6 hours at 50° C. Excess probes was washed at 50° C. in 2×SSC with 0.1% tween. The DNA probes were bound to avidin coated green fluorescence fluorospheres of a diameter of 40 nanometers (Molecular Probes, Portland Oreg.) in TNT for 1 hour at room temperature. Excess beads were washed off with TNT. Fluorescence was detected using an inverted microscope (using the 20×/0.400 LD Achroplan objective, on the Axiovert S100TV, with an arc mercury lamp HBO 100 W/2, Carl Zeiss, Oberkochen, Germany) coupled to a 768(H)×512(V) pixel-CCD camera (Princeton Instruments Inc. Trenton, N.J., USA). Exposure were 20 seconds through filter sets XF22 (Ex: 485DF22, Dichroic: 505DRLPO2 Em: 530DF30) and XF47 (Ex: 640DF20, Dichroic: 670DRLPO2 Em: 682DF22) from Omega Optical (Brattleboro Vt.) for FITC and Cy5 respectively. Data were analyzed using Winview software (Princeton Instruments Inc., Trenton N.J., USA). The numbers of colonies per field were counted in duplicate wells with image analysis software developed in house.

Example 3

Sequence Discrimination in Different Colonies Originated from Varying Ratios of 2 Different Covalently Bound Templates and a Colony Primer Covalent Binding of Templates and Colony Primer to the Solid Support (Plastic)

A colony primer (CP2: 5' pTTTTTTTTTTAGAAGGA-GAAGGAAAGGGAAAGGG) (SEQ ID NO:6), phosphorylated at its 5' terminus (Microsynth GmbH, Switzerland), was grafted onto Nucleolink plastic microtitre wells (Nunc, Denmark) in the presence of varying doses of the two templates A and B (prepared as described in example 1). Series of 8 wells were set up in triplicate with seven 1/10 dilutions of both templates starting with the highest concentration of 1 nM. Template dilutions are set up in opposite directions such that the highest concentration of one template coincides with the lowest of the other.

Microtitre wells, to which CP2 primer and both templates are covalently bound were prepared as follows. In each Nucleolink well, 30 µl of a 1 µM solution of the CP2 primer with varying concentrations of both templates diluted down from 1 nM in 10 mM 1 methyl-imidazole (pH 7.0) (Sigma Chemicals) were added. To each well, 10 µl of 40 mM 1-ethyl-3-(3-dimethylaminopropyl)-carbodiimide (pH 7.0) (Sigma Chemicals) in 10 mM 1-methyl-i imidazole (pH 7.0), was added to the solution of colony primer and templates. The wells were then sealed and incubated at 50° C. for 4 hours. After the incubation, the wells were rinsed three times with 50 µl of RS (0.4 N NaOH, 0.25% Tween 20), incubated 15 minutes with 50 µl RS, washed three times with 50 µl RS and three times with 50 µl TNT (100 mM TrisHCl pH 7.5, 150 mM NaCl, 0.1% Tween 20). Tubes were stored in TNT at 4° C.

Colonies Generation

Colony growing was initiated in each well with 20 µl of PCR mix; the four dNTPs (0.2 mM), 0.1% BSA, 0.1% Tween 20, 8% DMSO (dimethylsulfoxide, Fluka, Switzerland), 1× PCR buffer and 0.025 units/µl of AmpliTaq DNA polymerase (Perkin Elmer, Foster City, Calif.).

The wells were then placed in the thermocycler and growing was performed by incubating the sealed wells 5 minutes at 94° C. and cycling for 50 repetitions the following conditions: 94° C. for 30 seconds, 65° C. for 5 minutes, 72° C. for 5 minutes. After completion of this program, the wells were kept at 8° C. until further use. Prior to hybridization wells are filled with 50 µl TE (10 mM Tris, 1 mM EDTA, pH 7.4) heated at 94° C. for 5 minutes and chilled on ice before probe addition at 50° C.

Colonies Visualization

Probe: Two DNA fragments of 546 and 1405 base pairs corresponding to the sequences of the 3.2 Kb DNA fragment at the 5'- and 3'-termini were amplified by PCR using one biotinylated primer (see example 2). The two probes were denatured by heating at 94° C. for 5 minutes, quick-chilled into 1 M NaCl, 10 mM Tris pH 7.4 and allowed to bind to Strepatividin coated fluorospheres of diameter 0.04 µm labeled with different colors for 2 hours at 4° C. The probes bound to bead were diluted 20 fold in "easyhyb" solution prewarmed to 50° C. 20 µl of probes was added to each well containing denatured colonies.

Hybridization and detection: The hybridization was carried out at 50° C. for 5 hours. Excess probes was washed at 50° C. in 2×SSC with 0.1% SDS. Colonies were visualized by microscopy with a 20× objective, 20 second exposure and image analysis as described in example 2a. FIG. 4a shows the images of colonies made from both templates and negative controls. FIG. 4b shows the colonies from both templates at the same position in the same well visualised with two different colours and negative controls. FIG. 4c shows the coordinates of both colony types in a sub-section of a microscopy field. FIG. 4c demonstrates that colonies from different templates do not coincide.

Example 4

Covalent Binding of DNA Templates and Oligonucleotides on Glass Solid Supports

Aminosilane-derivatized glass slides have been used as solid support to covalently attach thiol-modified oligonucleotides probes using hetero-bifunctional cross-linkers. The reagents selected have thiol-reactive (maleimide) and amino-reactive groups (succinimidyl ester). Oligonucleotide attachment yields and stability of the immobilized molecules will be strongly dependent on the cross-linker stability towards the conditions of the different treatments performed. The reaction schemes of the DNA templates or oligonucleotides attachment on glass are described in FIG. 5.

The storage stability of glass slides prepared with the cross-linkers s-MBS and s-SIAB and its thermal stability have been evaluated. An important factor affecting the extent of hybridization of immobilized oligonucleotide probes is the density of attached probes (Beattie et al., 1995; Joss et al., 1997). We have studied this effect by varying the concentration of oligonucleotides during the immobilization and assaying the density of attached oligos by hybridization.

Materials and Methods

Microscope glass slides acid pre-treatment—Microscope glass slides (Knittel, Merck ABS) were soaked in basic Helmanex solution during 1 hour (HelmanexII$^R$ 0.25%, 1N NaOH). The slides were rinsed with water, immersed overnight in 1N HCl, rinsed again in water and treated 1 hour in sulfuric acid solution ($H_2SO_4/H_2O$, 1/1, v/v, with a small amount of fresh ammonium persulfate added). The slides were rinsed in water, in ethanol and finally with pure acetone. Glass slides are dried and stored under vacuum for further use.

Silanization of the surface—The pre-treated slides were immersed into a 5% solution of ATS (aminopropyltriethoxysilane, Aldrich) in acetone. Silanization was carried out at room temperature for 2 hours. After three washes in acetone (5 min/wash) the slides were rinsed once with ethanol, dried and stored under vacuum.

Cross-linker attachment—Cross-linkers, s-MBS and s-SIAB (respectively sulfo m-maleimidobenzoyl-N-hydroxysuccinimide ester, sulfo N-succinimidyl[4-iodoacethyl] aminobenzoate, Pierce, Rockford Ill.), are prepared as 20 mM solutions in PBS (phosphate-buffered saline, 0.1 M $NaH_2PO_4$, pH 7.2, 0.15 M NaCl). Silanized glass slides, on which 80 µL of cross-linker solution was applied, were covered by a cleaned micro cover glass and reacted for 5 hours at 20° C. The glass slides were rinsed in PBS, briefly immersed in water and rinsed in ethanol. Slides were then dried and stored under vacuum in the dark for further use.

Oligonucleotide Attachment—Oligonucleotides were synthesized with 5' modifications of a thiol (CP3 and CP4 Eurogentec, Brussels) or a phosphate moiety (CP1 and CP2, Eurogentec, Brussels) using standard phosphoramidite chemistry.

5'-thiol oligonucleotide primers (CP3 and CP4) were prepared as 100 µM solutions in a saline phosphate buffer (NaPi: 0.1M $NaH_2PO_4$ pH: 6.6, 0.15M NaCl) and drops of 1 µl applied on the functionalized glass slide (functionalized with cross-linker) for 5 hours at room temperature. Glass slides were kept under a saturated wet atmosphere to avoid evaporation. Glass slides were washed on a shaker in NaPi buffer. For thermal stability study glass slides were immersed 2 times in Tris buffer (10 mM, pH 8) for 5 min at 100° C. and directly immersed in 5×SSC (0.75 M NaCl, 0.075 M NaCitrate pH 7) at 4° C. for 5 min. Slides were stored in 5×SSC at 4° C. for further use.

5'-phosphate oligonucleotides primers (CP1 and CP2) were applied (1 µl drops) for 5 hours at room temperature to amino-derivatized glass as 1 µM solution in 10 mM 1-methyl-imidazole (pH 7.0) (Sigma Chemicals) containing 40 mM of 1-ethyl-3-(3-dimethylamino-propyl) carbodiimide (EDC, Pierce, Rockford Ill.). The slides were washed 2 times at 100° C. in Tris buffer (10 mM, pH 8) and directly immersed in 5×SSC at 4° C. for 5 min. Slides were stored in 5×SSC at 4° C. for further use.

Oligonucleotide and DNA Template Attachment

The 5'-thiol oligonucleotide primers (CP3 and CP4), and 5'-thiol template B' were mixed in a saline phosphate buffer (NaPi: 0.1M $NaH_2PO_4$ pH: 6.6, 0.15M NaCl). Concentration of DNA template varied from 0.001 to 1 µM and from 0.1 to 100 µM for primers but were optimized at 1 µM and 100 µM respectively for template and primers. The procedure described above for CP3 and CP4 attachment on functionalized glass surface was then followed.

The 5'-phosphate oligonucleotide primers (CP1 and CP2), and 5'-phosphate template B were mixed in a 10 mM 1-methyl-imidazole (pH 7.0)(Sigma Chemicals) solution containing 40 mM of 1-ethyl-3-(3-dimethylamino-propyl) carbodiimide (EDC, Pierce, Rockford Ill.). Concentration of DNA template varied from 0.001 to 10 nM and from 0.1 to 1 µM for primers, but were eventually optimized at 10 nM and 1 µM respectively for template and primers. The procedure described above for CP1 and CP2 attachment on amino-derivatized glass surface was followed.

Hybridization with fluorescent probes—Oligonucleotide probes, fluorescently labeled with Cy5 or FITC at their 5'end, were synthesized by Eurogentec (Brussels). To prevent non-specific hybridization, glass slides were incubated with a blocking solution (5×SSC, Tween 0.1%, BSA 0.1%) for 1 hour and washed on a shaker in 5×SSC (2 times, 5 min). Oligonucleotide probes were diluted at 0.5 µM in 5×SSC, Tween 0.1% and applied on the glass surface for 2 hours at room temperature. Glass slides were rinsed on a shaker at 37° C., once in 5×SSC for 5 min, and twice in 2×SSC containing 0.1% SDS for 5 minutes.

Hybridization with radiolabeled probes—Radiolabeled oligonucleotides complementary to covalently linked oligonucleotides were used as hybridization probes in order to quantify hybridization yields.

Oligonucleotides were enzymatically labeled at their 5' end terminus with [γ-$^{32}$P]dATP (Amersham, UK) using the bacteriophage T4 polynucleotide kinase (New England Biolabs, Beverly, Mass.). Excess (γ-$^{32}$P]dATP was removed with a Chroma Spin column TE-10 (Clontech, Palo Alto Calif.). Radiolabeled oligonucleotides (0.5 µM in 5×SSC, Tween 0.1%) were then applied onto derivatized slides for 2 hours at room temperature. Glass slides were rinsed on a shaker once in 5×SSC for 5 min and twice in 2×SSC, SDS 0.1% for 5 minutes at 37° C. After hybridization the specific activity was determined by scintillation counting.

Microscope observation—Glass slides were overlaid with 5×SSC solution and a micro cover glass. Fluorescence was detected using an inverted microscope model Axiovert S100TV, with an arc mercury lamp HBO 100 W/2 (Carl Zeiss, Oberkochen, Germany) coupled to a CCD camera equipped with a CCD array Kodak with a format 768(H)× 512(V) pixels; 6.91×4.6 mm overall, pixel size 9×9 µm2 (Princeton Instruments Inc. Trenton, N.J., USA). Exposition times were between 1 and 50 seconds using the objective LD Achroplan 20×/0.400 (Carl Zeiss, Oberkochen, Germany) and filter sets XF22 (Ex: 485DF22, Dichroic: 505DRLP02 Em: 530DF30) and XF47 (Ex: 640DF20, Dichroic: 670DRLP02 Em: 682DF22) from Omega Optical (Brattleboro Vt.) for FITC and Cy5 fluorophores respectively. Data were analyzed using Winview software (Princeton Instruments Inc., Trenton N.J., USA).

Results

Evaluation of Storage Stability Attachment and Thermal Stability

We evaluated the storage stability of glass plates prepared with s-MBS and s-SIAB. Since these reagents are sensitive towards hydrolysis, oligonucleotide attachment yields will be dependent on their stability. Amino-derivatized glass plates were functionalized with freshly prepared crosslinking reagents, s-MBS and s-SIAB. The functionalized slides were stored after cross-linking attachment for 10 days in a dessicator under vacuum in the dark at room temperature. After this time, stored slides (t=10 days) and freshly reacted slides with the cross-linker reagents (t=0) were assayed. The results obtained after reaction of a thiol-oligonucleotide and hybridization of a complementary fluorescent probe were compared for both chemistries at t=0 and time=10 days.

Once immobilized, the s-SIAB-functionalized slides are fully stable after 10 days storage as evidenced by the same yields of hybridization obtained at t=0 and t=10 days. In contrast, coupled s-MBS to glass was found to be less stable with a 30% loss in yield of oligonucleotide attachment and hybridization after 10 days storage. In conclusion, s-SIAB functionalized slides are preferred as they can be prepared in advance and stored dry under vacuum in the dark for at least ten days without any reduction in probe attachment yield.

To evaluate the thermal stability of oligonucleotides attached to glass, the slides were subjected to two 5-min treatments at 100° C. in 10 mM Tris-HCl, pH 8. The remaining oligonucleotide still immobilized after washes was assayed by hybridization with a fluorescently labeled complementary oligonucleotide. About 14% of the molecules attached are released for s-SIAB glass slides and 17% for S-MBS glass slides after the first 5 minutes wash, but no further release was detected in the second wash for both chemistries (TABLE 1A). These results are encouraging compared to those obtained by Chrisey et al. 1996, where a release of more than 62% of oligonucleotides attached on fused silica slides via the crosslinker SMPB (Succinimidyl 4-[p-maleimidophenyl] butyrate) was measured after a 10 min treatment in PBS at 80° C.

TABLE 1A

Thermal stability study

| | Hybridisation results (arbitrary units, normalised to 100%) | | |
|---|---|---|---|
| | Freshly attached | After 5 min wash at 100° C. | After 2 × 5 min wash at 100° C. |
| s-MBS | 80 ± 6 | 69 ± 4 | 73 ± 4 |
| s-SIAB | 100 ± 9 | 84 ± 8 | 87 ± 3 |

Oligonucleotides were attached to glass slides functionalized with either s-MBS or s-SIAB. Attached oligonucleotides were assayed by hybridization with a fluorescently-labeled complementary oligonucleotide. Fluorescence signal is normalized at 100 for the highest signal obtained. Averaged values of triplicate analyses are reported.

Hybridization as a Function of Probe Attachment

We have studied the extent of hybridization of covalently bound oligonucleotide probes as a function of the surface coverage of attached oligonucleotides using the s-MBS, s-SIAB cross-linkers and EDC-mediated reactions. The concentration of oligonucleotides applied for immobilization was 1 µM for EDC and has been varied between 1 and 800 µM for crosslinkers, the surface density was assayed by hybridization with $^{32}$P-labeled probes. The optimal concentration for primer attachment using the heterobifunctional cross-linkers was 500 µM which equates with a surface density of hybridized molecules of 60 fmol/mm$^2$ for s-MBS and 270 fmol/mm$^2$ for s-SIAB. Similar coverage density as s-MBS was obtained using EDC/Imidazole-mediated attachment of 5'-phosphate oligonucleotides to aminosilanised glass. However, only 1 µM solutions of oligonucleotide were necessary to attain the same attachment yield, this represents a 500-fold excess of oligonucleotide to be attached for the s-MBS chemistry compared to the EDC/imidazole coupling strategy (Table 1B).

TABLE 1B

Hybridization as a function of probe attachment

| Conc. of oligonucleotide used for attachment (µM) | Oligo hybridized (fmol/mm$^2$) | | |
|---|---|---|---|
| | s-MBS | s-SIAB | EDC |
| 1 | NT | NT | 50 |
| 100 | 10 | 100 | NT |
| 500 | 60 | 270 | NT |

Oligonucleotides were attached to glass slides functionalized with either s-MBS or s-SIAB or via mediated activating reagent EDC. Attached oligonucleotides were assayed by hybridization with a radiolabeled complementary oligonucleotide. The specific activity and therefore the density of hybridized molecules were determined by scintillation liquid. NT: not tested The 60 fmol/cm$^2$ surface density corresponds to an average molecular spacing between bound oligonucleotides of 8 nm. According to our results, a coverage density of 30 fmol/mm$^2$ (spacing of 20 nm) is sufficient to obtain DNA colonies. This yield can be obtained by immobilizing primers at 100 µM using the heterobifunctional cross-linker s-SIAB or 1 µM probes using the EDC-mediated approach. The hybridization densities we have obtained are in the range of the highest densities obtained on glass slides of other grafting protocols previously reported (Guo et al-1994, Joss et al-1997, Beattie et al—1995).

DNA Colony Generation on Glass: Colonies Formation is Dependent on the Length, the Concentration of Template and the Concentration of Primers Theoretically, DNA colony formation requires an appropriate density of primers attached on the surface corresponding to an appropriate length of the DNA template. For optimal DNA colony generation, it is important to define the range of densities of the bound primers and templates, as well as the stoichiometric ratio between template and primer.

Materials and Methods

Glass Slide Preparation

Glass slides were derivatized and functionalized as described above (Materials and methods). DNA colony primers were CP1 and CP2. The colony templates were prepared as described in example 1 for template B', but using primers TPB3 and TPB2. The modified colony primers and templates were applied on glass surface at varying concentrations of both colony primer and colony template.

Generation of Colonies

Glass slides stored in 5×SSC were washed in micro-filtered water to removed salts. Colony growing was initiated on glass surface with a PCR mix; the four dNTP (0.2 mM), 0.1% BSA, 0.1% Tween 20, 1×PCR buffer and 0.05 U/µl of AmpliTaq DNA polymerase (Perkin Elmer, Foster City, Calif.). The PCR mix is placed in a frame seal chamber (MJ Research, Watertown, Mass.). The slides were placed in the thermocycler (The DNA Engine, MJ Research Watertown, Mass.) and thermocycling was as carried out as follows: step 1 at 94° C. for 1 min, step 2 at 65° C. for 3 minutes, step 3 at 74° C. for 6 min and this program is repeated 50 times. After completion of this program the slides are kept at 6° C. until further use.

Digestion of Double Strand DNA Colonies

The glass surface containing the DNA was cut with a restriction nuclease by overlaying with the restriction enzyme in a digestion 1× buffer. The reaction was run twice for 1 h30 at 37° C. Double strand DNA colonies were denatured by immersing slides 2 times in tris buffer (10 mM, pH 8) at 100° C. for 5 min, followed by a rinse in 5×SSC at 4° C. Slides were stored in 5×SSC for further use.

Hybridization of One Strand DNA Colonies

To prevent non-specific hybridization, glass slides were incubated with a blocking solution (5×SSC, 0.1% Tween, 0.1% BSA) for 1 hour and the slides rinsed in 5×SSC (2 times, 5 min). Fluorescently Cy5 5' end labeled oligonucleotide (Eurogentec, Brussels) were diluted at 0.5 µM in SSC 5×, Tween 0.1% and applied to the glass surface for at least 2 hours. Glass slides are rinsed on a shaker once in SSC 5× for 5 min and twice in SSC 5×, SDS 0.1% 5 minutes at 37° C.

The glass slides were visualized as previously described.

We have previously observed that the extent of hybridization is a function of the density of oligonucleotide attachment. A similar study with bound DNA templates has shown that colony formation is also a function of the concentration of template attached on glass slide. Depending on the chemistry used for oligonucleotide and template attachment, the optimal concentration of template is 1 µM for the bi-functional crosslinkers, s-MBS (FIG. 6B), and 1 nM for EDC carbodiimide (FIG. 6A). Interestingly, a higher concentration of template does not enhance number of colonies for EDC chemistry and a plateau corresponding to a maximal number of colonies seems to be reached.

We have studied colony formation (number) as a function of the concentration of primers, concentration of the DNA template applied on the surface and the length of the DNA template.

We have also evaluated the number of copy of template in each colony. The quantification was based on fluorescence detection with Cy5-, Cy3- or fluorescein-labeled fluorophores supplemented with an anti-bleaching reagent (Prolong, Molecular Probes, Portland Oreg.). The calibration has been done by hybridization experiments on primers attached to the surface as the exact density corresponding has been determined by radioactivity Example 5

Colony In-situ DNA Sequencing

Glass slides (5 mm diameter Verrerie de Carouge, Switzerland) were first placed into a Helmanex 0.2% (in $H_2O$), NaOH 1N bath for 1 h at room temperature, rinsed with distilled water, rinsed in pure Hexane, rinsed again two times with distilled water and treated with HCl 1M over night at room temperature. Then, they were rinsed two times in distilled water, and treated with $H_2SO_4$ (50%)+$K_2S_2O_8$ for 1 h at room temperature. They were rinsed in distilled water, then two times in Ethanol. Glass slides were derivatized with ATS (as described in example 4).

Colony primers CP1 (5'-pTTTTTTTTTTCACCAAC-CCAAACCAACCCAAACC) (SEQ ID NO:5) and CP2 (5'-pTTTTTTTTTAGAAGGA-GAAGGAAAGGGAAAGGG) (SEQ ID NO:6) which are 5'phosphorylated (Microsynth GmbH, Switzerland) and DNA template B (prepared as described in example 1) were 5' covalently attached onto 5 mm diameter glass slides (Verrerie de Carouge, Switzerland) to a final concentrations of 1 µM and 10 nM respectively, as follows: 2 nmoles of each primer were added to 0.2 nmoles of template in 1 ml of solution A (41 µl of Methylimidazole (Sigma, #M-8878) in 50 ml H20, pH adjusted to 7 with HCl) and then mixed 1:1 with solution D (0.2 mM EDC in 10 ml of solution A). On both glass slides sides, 3.5 µl of the mixture were loaded, and incubated over night at room temperature. The glass slides were then briefly rinsed with 5×SSC buffer and placed at 100° C. in 10 mM Tris buffer pH 8.0 for 2×5'.

Non specific sites on glass were blocked with Bovine Serum Albumin (BSA, Boehringer Mannheim GmbH, Germany, #238040) at 1 mg/ml in 5×SSC buffer for 1 h at room temperature and then rinsed with distilled water.

Glass slides were then individually placed onto a Microamp™ reaction tube (Perkin Elmer) containing 170 µl of PCR mix, and DNA colonies were then generated using Taq polymerase (AmpliTaq, PE-Applied Biosystems Inc., Foster City Calif.) with 50 cycles (94C/60", 60C/3', 72C/6') in a MTC 200 thermo-cycler (MJ Research, Watertown, Mass.). Each slide was digested twice using 1.3 units of Pvu II (Stratagene) in NEB 2 buffer (New England Biolabs) for 45 minutes at 37° C. After digestion, the tubes were placed at 100° C. in 10mM Tris buffer pH 8.0 for 2×5', then blocked with filtered (Millex GV4, Millipore) 1 mg/ml BSA in 2×SSC buffer for 30' at room temperature and rinsed first in 2×SSC 0.1% SDS buffer then in S×SSC buffer. Each slide was incubated over night at room temperature with a 5×SSC/0.1% Tween 20 buffer containing 1 µM of the sequencing primer p181(CGACAGCCG-GAAGGAAGAGGGAGC) (SEQ ID NO: 18) overnight at room temperature. Controls without primer were kept in 5×SSC 0.1% Tween 20 buffer. Glass slides were washed 2 times in S×SSC 0.1% SDS at 37C for 5' and rinsed in S×SSC. Primer p181 can hybridize to template B' and the sequence following p1B1 is CAGCT . . . . In order to facilitate focusing, green fluorescent beads have been adsorbed to the bottom of the well by incubating each well with 20 μl of a 1/2000 dilution of 200 nm yellow/green fluorescent, streptavidin coated FluoSpheres(®) (Molecular Probes, Eugene, Oreg.) in SX SSC for 20" at room temperature.

After hybridization with the primer, 2 μl of a solution containing 0.1% BSA, 6 mM dithiotreitol (Sigma Chemicals), 5 μM Cy5™-dCTP or 5 μM Cy5™-dUTP (Amersham, UK) and 1× Sequenase reaction buffer is added to each slide. The addition of the Cy5™-nucleotide is initiated with the addition of 1.3 unit of T7 Sequenase™ DNA polymerase (Amersham, UK) for two minutes at room temperature. The wells are washed 2 times in 5×SSC/0.1% SDS bath for 15' and rinsed with 5×SSC buffer.

The samples are observed using an inverted microscope (Axiovert S100TV, Carl Zeiss AG, Oberkochen, Germany) equipped with a Micromax 512×768 CCD camera and Winview software (Princeton Instruments, Trenton, N.J.). For focusing, a 20× objective and a XF 22 filter set (Omega Optical, Brattleboro, Vt.) were used, and for observing Cy5™ incorporation on the samples, a 20× objective and a XF47 filter set (Omega Optical) with a 50 second exposure using a 2×2 pixel binning. The yellow/green FluoSpheres® (approximately 100/field of view) do not give a detectable signal using the XF47 filter set and 50 second exposure (data not shown). The photos are generated by the program, Winview (Princeton Instruments).

FIG. 7A shows the result after incubation with Cy5™-dCTP on a sample that has not been incubated with primer p181. One will appreciate 5 blurry spots can be observed, indicating that no dramatic spurious effect is taking place (such as Cy5™-dCTP aggregate precipitation, adsorption or simply non specific incorporation to the DNA in the colonies or on the surface). FIG. 7B shows the result after incubation with Cy5™-dUTP on a sample that has been incubated with primer p181. One will appreciate that no fluorescent spot can be observed, indicating that the incorporation of a fluorescent base cannot take place in detectable amounts when the nucleotide proposed for incorporation does not correspond to the sequence of the template following the hybridized primer. FIG. 7C shows the result after incubation with Cy5™-dCTP on a sample that has been incubated with primer p181. One will appreciate that many fluorescent spots can be observed, indicating that the incorporation of a fluorescent base can indeed take place in detectable amounts when the nucleotide proposed for incorporation does correspond to the sequence of the template following the hybridized primer. To summarize, we showed that it is possible to incorporate on a sequence specific manner fluorescent nucleotides into the DNA contained in the colonies and to monitor this incorporation with the apparatus and method described. However, this is only a example. One will appreciate that if desired the incorporation of a fluorescent base could be repeated several times. As this is done on a sequence specific manner, it is thus possible to deduce part of the sequence of the DNA contained in the colonies.

Example 6

5' mRNA Sequence Tag Analysis

The most accurate way to monitor gene expression in cells or tissues is to reduce the number of steps between the collection of the sample and the scoring of the mRNA. New methods for rapidly isolating mRNA are commercially available. The most efficient methods involve the rapid isolation of the sample and immediate disruption of cells into a solution of guanidinium hydrochloride, which completely disrupts proteins and inactivates RNAses. This is followed by the purification of the mRNA from the supernatant of the disrupted cells by oligo-dT affinity chromatography. Finally, 5'-capped mRNA can be specifically targeted and transformed into cDNA using a simple strategy (SMART cDNA synthesis, Clontech, Palo Alto).

This method allows the synthesis of cDNA copies of only the translationally active, 5'-capped mRNA. By combining the above rapid methods of mRNA isolation and cDNA preparation with the grafted-template method of DNA colony generation described in the present application, we have an approach for the high-throughput identification of a large number of 5' mRNA sequence tags. The advantage of our invention is the possibility to sequence a large number of cDNA by directly grafting the product of the cDNA synthesis reaction, amplifying the cDNA into thousands of copies, followed by the simultaneous in situ sequencing of the cDNAs.

Materials and Methods:

Synthetic oligonucleotides and plasmids—Oligonucleotides were synthesized with 5'-phosphates by Eurogentec or Microsynth. Plasmids containing partial coding and 3'-untranslated sequences of the murine potassium channel gene, mSlo, following the T3 RNA polymerase promoter were generated by standard methods.

mRNA synthesis—mSlo plasmids were linearized at a single SalI or SacI restriction nuclease site following the poly A+ sequence in the plasmid. After treatment of the cut plasmid with proteinase K, linear plasmid DNA was extracted once with phenol/CH$_3$Cl/isoamyl alcohol and precipitated with ethanol. The DNA precipitate was re-dissolved in H$_2$O at a concentration of 10 μg/μl. Synthetic mRNA capped with the 5'-methylguanosine were synthesized by the mMessage mMachine in vitro mRNA synthesis kit as per manufacturer instructions (Ambion, Austin Tex.). Synthetic mRNA was stored at 80° C.

Enzymes—Restriction enzymes were obtained from New England Biolabs (Beverly, Mass.).

cDNA synthesis—Synthetic mRNA was mixed with mouse liver poly A+ mRNA at different molar ratios (1:1, 1:10, 1:100) and cDNA synthesis on the mixture of synthetic and mouse liver mRNA was performed using the "SMART PCR cDNA synthesis kit" {Clontech, Palo Alto Calif.) with some minor modifications. In a cDNA reaction, approximately 1 μg of the mRNA mixture was mixed with the primer CPS, having at the 5' -end the sequence of CPβ, (5'p-AGAAGGA-GAAGGAAAGGGAAAGGGTTTTTTTTTTTTTTTNN) (SEQ ID NO:9). This primer has been used to make the 1st strand cDNA synthesis. For the 2nd strand synthesis, the "SMART" technique has been used. The basis of the SMART synthesis is the property of the Moloney murine viral reverse transcriptase to add three to five deoxycytosine residues at the 3'-termini of first strand cDNA, when the mRNA contains a 5'-methylguanosine-cap (SMART user 35 manual, Clontech, Palo Alto Calif.). A CP6 primer, which contains the sequence of CP~ plus AAAGGGGG at the 3' end, (5'p-AGAAGGAGAAGGAAAGGGAAAGGGGG) (SEQ ID NO: 10) has been used for the 2nd strand cDNA synthesis. Buffer and SUPERSCRIPT™II RNase H-reverse transcriptase from Moloney murine leukemia virus (Life Technologies, Ltd.) were used as described in the instructions and the reaction was carried out at 42° C. for 1 hr. The cDNA was assayed by PCR using the primer p251, which contains a fragment of the CPβ sequence, (5'-GA-GAAGGAAAGGGAAAGG) (SEQ ID NO: 19) with Taq DNA polymerase (Platinum Taq, Life Technologies, Ltd.).

DNA probes and hybridization—$^{32}$Biotinylated and $^{32}$P-radiolabelled DNA probes specific for the mSlo DNA sequence were synthesized with a 5'-biotinylated primer and a normal downstream primer by PCR on the template (mSlo plasmid DNA). The probe incorporated α[$^{32}$P]-dCTP (Amersham, Amersham UK) at a ratio of 300:1 (α[$^{32}$P]-dCTP to dCTP) in the PCR reaction, with a final concentration of the four deoxynucleoside triphosphates of 50 μM. The resulting biotinylated and radiolabelled DNA probe was desalted over a Chromaspin-1000 column (Clontech, Palo Alto Calif.). The DNA probes were hybridized to the samples in "easy-hyb" buffer (Boehringer-Mannheim, Germany), using the following temperature scheme (in the MTC200 thermocycler): 94° C. for 5 minutes, followed by 68 steps of 0.5° C. decrease in temperature every 30 seconds (in other words, the temperature is decreased down to 60° C. in 34 minutes), using sealed wells. The samples are then washed 3 times with 200 μl of TNT at room temperature. The wells are then incubated for 30 minutes with 50 μl TNT containing 0.1 mg/ml BSA (New England Biolabs, Beverly, Mass.). Then the wells are incubated 5 minutes with 15 μl of solution of red fluorescent, streptavidin-coated, 40 nanometer microspheres (Molecular Probes, Portland, Oreg.). The solution of microspheres is made of 2 μl of the stock solution of microspheres, which have been sonicated for 5 minutes in a 50 W ultra-sound water-bath (Elgasonic, Bienne, Switzerland), diluted in 1 ml of TNT solution containing 0.1 mg/ml BSA and filtered with Millex GV4 0.22 μm pore size filter (Millipore, Bedford, Mass.).

DNA colony visualization—The stained samples are observed using an inverted Axiovert 10 microscope using a 20× objective (Carl Zeiss AG, Oberkochen, Germany) equipped with a Micromax 512×768 CCD camera (Princeton instruments, Trenton, N.J.), using a PB546/FT580/LP590 filter set, and 10 seconds of light collection. The files are converted to TIFF format and processed in the suitable software (PhotoPaint, Corel Corp. Ltd, Dublin, Ireland). The processing consisted in inversion and linear contrast enhancement, in order to provide a picture suitable for black and white printout on a laser printer.

Results

Synthetic mRNA and cDNA Synthesis—Following cDNA synthesis, the cDNA was checked in a PCR using the p251 primer (generated at each end of the first strand cDNA) for the correct lengths of products as assayed by agarose gel electrophoresis. The synthetic mSlo mRNA was diluted into the liver mRNA, which was evidenced by the decreasing intensity of the mSlo-specific band and the increase of a non-specific smear of liver cDNA.

Detection and Quantification of DNA Colonies—DNA colonies were assayed using fluorescent imaging CCD microscopy or scintillation counting. The numbers of fluorescently detectable colonies increased as a function of the amount of grafted template, as shown in FIG. 6. This increase was mirrored by the amount of P-radiolabel detected.

With radiolabelled probes it is possible to detect mRNA copies at about 1:100. But with fluorescent microscopic CCD imaging technology, one can detect mRNA to a dilution of 1:10000.

Example 7

Covalent Binding of Primer to the Solid Support (Plastic)

Preparation of DNA colonies—The 5'p-cDNA was mixed with different concentrations of the solid phase colony primer, CP2 (5'p-TTTTTTTTTTAGAAGGA-GAAGGAAAGGGAAAGGG) (SEQ ID NO:6) and chemically bound to Nucleolink PCR tubes (NUNC) following manufacturer instructions. DNA colonies were then generated using Taq polymerase (AmpliTaq Gold, PE-Applied Biosystems Inc., Foster City Calif.) with 30 cycles (94C/30", 65C/1', 72C/1.5') in a MTC 200 thermo-cycler (MJ Research, Watertown, Mass.).

Stability of Bound Oligonucleotides Under PCR Colony Generation Conditions

Oligonucleotide primers were attached onto Nucleolink plastic microtitre wells (Nunc, Denmark) in order to determine optimal coupling times and chemistries. Oligonucleotides; CP2 (5'-(phosphate)-TTTTTTTTTTAGAAGGA-GAAGGAAAGGGAAAGGG) (SEQ ID NO:6), CP8(5' (aminohexamethylene)-TTTTTTTTTTAGAAGGA-GAAGGAAAGGGAAAGGG) (SEQ ID NO:6), CP9 (5' (hydroxyl)-TTTTTTTTTTAGAAGGA-GAAGGAAAGGGAAAGGG) (SEQ ID NO:6), CP10 (5' -(dimethoxytrityl)TTTTTTTTTTAGAAGGA-GAAGGAAAGGGAAAGGG) (SEQ ID NO:6) and CP11 (5' (biotin)-TTTTTTTTTTAGAAGGA-GAAGGAAAGGGAAAGGG) (SEQ ID NO:6), (Microsynth GmbH, Switzerland), were attached to Nucleolink microtitre wells as follows (8 wells each); to each well 20 μl of a solution containing 0.1 μM oligonucleotide, 10 mM 1-methyl-imidazole (pH 7.0) (Sigma Chemicals) and 10 mM 1-ethyl-3-(3-dimethylaminopropyl)carbodiimide (pH 7.0) (Sigma Chemicals) in 10mM 1-methyl-imidazole. The wells were then sealed and incubated 50° C. for varying amounts of time. The coupling reaction was terminated at specific times by rinsing twice with 200 μl of RS (0.4 N NaOH, 0.25% Tween 20) and twice with 200 μl TNT (100 mM TrisHCl pH 7.5, 150 mM NaCl, 0.1% Tween 20). Tubes were dried at 50° C. for 30' and were stored in a sealed plastic bag at 4° C.

Stability was tested under colony growing conditions by adding a PCR mix (20 μl of four dNTPs (0.2 mM), 0.1% BSA, 0.1% Tween 20, 8% DMSO (dimethylsulfoxide, Fluka, Switzerland), IX PCR buffer). The wells were then placed in the thermocycler and for 33 repetitions under the following conditions: 94° C. for 45 seconds, 60° C. for 4 minutes, 72° C. for 4 minutes. After completion of this program, the wells were rinsed with 5×SSC, 0.1% Tween 20 and kept at S° C. until further use. Prior to hybridization wells are filled with 50 μl 5×SSC, 0.1% Tween 20 heated at 94° C. for 5 minutes and stored at RT. Probe: Oligonucleotide probes, R57 (5' (phosphate)GTTTGGGTTG-GTTTGGGTTGGTG, control probe) (complement to SEQ ID NO:2) and R5S (5'(phosphate)-CCCTTTCCCTTTCCT-TCTCCTTCT (complement of DEQ ID NO:1), which is complementary to CP2, CPS, CP9, CP10 and CP11) were enzymatically labeled at their 5' end terminus with γ-$^{32}$P dATP (Amersham, UK) using the bacteriophage T4 polynucleotide kinase (New England Biolabs, Beverly, Mass.). Excess 32P d.ATP was removed with a Chroma Spin column TE-10 (Clontech, Palo Alto Calif.). Radiolabeled oligonucleotides (0.5 μMin S×SSC, 0.1% Tween 20) were then hybridized to the oligonucleotide derivatized Nucleolink wells at 37° C. for two hours. The wells were washed 4 times with 5×SSC, 0.1% Tween 20 at room temperature, followed by a wash with 0.5×SSC, 0.1% Tween 20 for 15' at 37° C. Wells were then assayed for bound probe by scintillation counting.

Results

There is a marked difference in the rate and specificity of oligonucleotide coupling depending on the nature of 5'-functional group on the oligonucleotide. Oligonucleotides carrying the 5'-amino group coupled approximately twice as fast as oligonucleotides functionalized with a 5'-phosphate group (see Table 2 and FIG. 8). In addition, the control oligonucleotides functionalized with 5'hydroxyl, 5'-DMT or 5'-biotin all coupled at rates similar to that of the 5'-phosphate, which questions the 5'specific nature of the chemical attachment using the 5'-phosphate group.

TABLE 2

|  | 5'-phosphate | 5'-amino | 5'-hydroxyl | 5'-DMT | 5'-biotin |
|---|---|---|---|---|---|
| Ka (min-1) | 0.0068 | 0.0135 | 0.0063 | 0.0070 | 0.0068 |
| Attached oligonucleotide (fmol/well) | 608 | 1344 | 542 | 602 | 650 |
| PCR stability (% remaining) | 56 | 69 | 66 | 66 | 62 |

The invention claimed is:

1. A method comprising the following steps:
   (1) forming at least one first nucleic acid template comprising at least one nucleic acid to be amplified, wherein said at least one nucleic acid contains (a) an oligonucleotide sequence Y and a means for attaching the at least one first nucleic acid template to a solid support at its 5' end and (b) an oligonucleotide sequence Z at its 3' end;
   (2) mixing said at least one first nucleic acid template with one or more colony primers X, each of which carries a means for attaching one of the one or more colony primers X to the solid support at its 5' end, in the presence of the solid support such that the 5' ends of both the at least one first nucleic acid template and the one or more colony primers X bind to the solid support and resulting in at least one bound first template and one or more bound colony primers, wherein at least a subset of the one or more colony primers X can hybridize to the oligonucleotide sequence Z;
   (3) performing one or more nucleic acid amplification reactions on the at least one bound first nucleic acid template, so that a first nucleic acid colony is generated, wherein the first nucleic acid colony comprises multiple copies of the at least one bound first nucleic acid template; and
   (4) performing at least one step of sequence determination of one or more of the multiple copies of the at least one bound first nucleic acid template while the one or more of the multiple copies of the at least one bound first nucleic acid template is bound to the solid support.

2. The method of claim 1, wherein the oligonucleotide sequence Z is complementary to the oligonucleotide sequence Y and the oligonucleotide sequence of the one or more colony primers X is the same as the oligonucleotide sequence Y.

3. The method of claim 1, wherein the one or more colony primers X comprise two different colony primers X, and wherein the two different colony primers X are mixed with said at least one first nucleic acid template in step (2), and wherein the sequence of one of the two different colony primers X is capable of hybridizing to the oligonucleotide sequence Z, and wherein the sequence of the other of the two different colony primers X is the same as the oligonucleotide sequence Y.

4. The method of claim 1, wherein the step of sequence determination involves incorporation and detection of labelled nucleotides on the one or more of the multiple copies of the at least one bound first nucleic acid template.

5. The method of claim 4, wherein the method further comprises
   (1') forming additional nucleic acid templates, wherein each of the additional nucleic acid templates contains (a) the oligonucleotide sequence Y and a means for attaching one of the additional nucleic acid templates to the solid support at its 5' end, and (b) the oligonucleotide sequence Z at its 3' end;
   (2') mixing each of the additional nucleic acid templates with the one or more colony primers X in the presence of the solid support such that the 5' ends of both each of the additional nucleic acid templates and the one or more colony primers X bind to the solid support and resulting in bound additional templates and the one or more bound colony primers, wherein at least a subset of the one or more colony primers X can hybridize to the oligonucleotide sequence Z;
   (3') performing one or more nucleic acid amplification reactions on the bound additional nucleic acid templates, so that one or more additional nucleic acid colonies are generated in addition to the first nucleic acid colony, each of the one or more additional nucleic acid colonies comprising multiple copies of one of the bound additional nucleic acid templates, each of the additional nucleic acid templates having a different nucleic acid sequence, and wherein the sequences of the bound additional nucleic acid templates and the sequence of the bound first template are determined simultaneously.

6. The method of claim 4, further comprising an additional step of visualising the first colony.

7. The method of claim 6, wherein the step of visualising the first colony involves the use of a labelled or unlabelled nucleic acid probe.

8. The method of claim 1, wherein said 5' ends of both the at least one first nucleic acid template and the one or more colony primers X are covalently bound to the solid support.

9. The method of claim 8, wherein the at least one first nucleic acid template and the one or more colony primers X comprise a chemically modifiable functional group that covalently binds the at least one first nucleic acid template and the one or more colony primers X to the solid support.

10. The method of claim 9, wherein said chemically modifiable functional group is a phosphate group, a carboxylic or aldehyde moiety, a thiol, a hydroxyl, a dimethoxytrityl (DMT), or an amino group.

11. The method of claim 10, wherein said chemically modifiable functional group is an amino group.

12. The method of claim 1, wherein said solid support is selected from the group consisting of latex beads, dextran beads, polystyrene and polypropylene surfaces, polyacrylamide gel, gold surfaces, and silicon wafers.

13. The method of claim 1, wherein the solid support is glass.

14. The method of claim 5, wherein the densities of the first nucleic acid colony and the additional nucleic acid colonies on the solid support are 10,000/mm$^2$ to 100,000/mm$^2$.

15. The method of claim 1, wherein the density of the one or more bound colony primers X on the solid support is at least 1 fmol/mm$^2$.

16. The method of claim 1, wherein the density of the at least one bound first nucleic acid template in the first nucleic acid colony is 10,000/mm$^2$ to 100,000/mm$^2$.

* * * * *